United States Patent
Yanai et al.

(10) Patent No.: US 7,491,526 B2
(45) Date of Patent: Feb. 17, 2009

(54) INCUBATOR AND CULTURE DEVICE

(75) Inventors: Tsuyoshi Yanai, Sagamihara (JP); Yuji Takamiya, Sagamihara (JP); Hiroki Hibino, Hachioji (JP)

(73) Assignee: Olympus Corporation, Tokyo (JP)

( * ) Notice: Subject to any disclaimer, the term of this patent is extended or adjusted under 35 U.S.C. 154(b) by 722 days.

(21) Appl. No.: 10/513,616

(22) PCT Filed: Aug. 15, 2003

(86) PCT No.: PCT/JP03/10382

§ 371 (c)(1),
(2), (4) Date: Nov. 4, 2004

(87) PCT Pub. No.: WO2004/016728

PCT Pub. Date: Feb. 26, 2004

(65) Prior Publication Data

US 2005/0239196 A1    Oct. 27, 2005

(30) Foreign Application Priority Data

Aug. 19, 2002  (JP)  ............................. 2002-238076
Sep. 6, 2002   (JP)  ............................. 2002-261128

(51) Int. Cl.
*C12M 1/00* (2006.01)
(52) U.S. Cl. .................................. 435/289.1
(58) Field of Classification Search ................ 435/289.1
See application file for complete search history.

(56) References Cited

U.S. PATENT DOCUMENTS 4,937,194 A    6/1990  Pattillo et al.
5,739,019 A *  4/1998  Walker et al. ................ 435/174
5,846,828 A   12/1998  Peterson et al.
5,863,502 A    1/1999  Southgate et al.
5,976,300 A   11/1999  Buchanan et al.
6,146,890 A   11/2000  Danon
2003/0054335 A1  3/2003  Taya et al.

FOREIGN PATENT DOCUMENTS

| JP | 61-290035 | 12/1986 |
| JP | S63-503201 | 11/1988 |
| JP | 10-84942 | 4/1998 |
| JP | 10-206313 | 8/1998 |
| JP | 2001-517062 | 10/2001 |
| WO | WO 96/01045 | 1/1996 |
| WO | WO 9601045 A1 * | 1/1996 |
| WO | WO 01/75070 A1 | 10/2001 |

* cited by examiner

*Primary Examiner*—Walter D Griffin
*Assistant Examiner*—Bobby Ramdhanie
(74) *Attorney, Agent, or Firm*—Scully, Scott, Murphy & Presser, P.C.

(57) ABSTRACT

Contamination by dust particles, bacteria and so forth in each processing step can be reduced by a simple constitution. A culture vessel is used in which a medium vessel in which a medium is sealed and a waste medium vessel capable of housing the fluid in a main culture vessel are connected to the main culture vessel by connecting lines capable of restricting the flow of fluid between them in a state in which they are sealed from the outside. A culture apparatus is composed in which the inner volume of each vessel is variable, and is provided with a case provided with indentations for housing each vessel, and a pressing means that contracts the vessels housed in the indentations by applying external pressure.

3 Claims, 24 Drawing Sheets

INCUBATOR AND CULTURE DEVICE

TECHNICAL FIELD

The present invention relates to a culture vessel and culture apparatus for culturing cells.

BACKGROUND ART

In order to culture cells, a plurality of steps are carried out in order, including an extraction step in which the cells to be cultured are extracted from bone marrow fluid or other liquid extracted from a patient, a medium preparation step in which a medium suitable for the cells to be cultured is prepared, a primary culturing step in which the extracted cells are placed in a medium in a suitable culture vessel and subjected to predetermined culturing conditions, and a secondary culturing step in which the primary cultured cells are mixed into a body tissue supplement material followed by additional culturing.

This type of cell culturing has conventionally been considered to be carried out in a clean room for which particle levels are controlled after sealing the entire culture (see, for example, Japanese Examined Patent Application, Second Publication No. 3-57744, page 2, column 3).

Namely, an air flow is formed inside a clean room by which air flows from the ceiling towards the floor, and in the case dust particles and so forth are generated in each treatment step, the dust particles are carried towards the floor by the flow of air and then collected by a dust collector disposed beneath the floor. Robot arms are installed within the clean room, and cells can be transferred between each step.

However, in the case of carrying out all of the treatment steps within a clean room in this manner, since the space in which each step is carried out is continuous, dust particles generated in one step have the potential for contaminating cells allocated to the next step. Thus, in the case of simultaneously culturing a plurality of cells, problems result due to the occurrence of contamination between cells or contamination of added substances.

In consideration of the aforementioned circumstances, the object of the present invention is to provide a culture vessel and culture apparatus capable of reducing contamination by dust, bacteria and so forth in each treatment step using a simple constitution.

DISCLOSURE OF THE INVENTION

The present invention provides a culture vessel comprising: at least one medium vessel having one main culture vessel in which a medium is sealed, and at least one waste medium vessel capable of housing the fluid in the culture vessel; said medium vessel and culture vessel being sealed from the outside by connecting lines capable of restricting the flow of fluid between the vessels.

In a culture vessel having the aforementioned constitution, cells are placed in the main culture vessel, and restriction on the flow of fluid in the connecting line between the medium vessel and main culture vessel is removed to allow medium to flow from the medium vessel into the main culture vessel through the connecting line. By then again restricting the flow of fluid in the aforementioned connecting line while in this state, the inside of the main culture vessel can be sealed from other vessels. As a result, cells can be cultured in the main culture vessel while sealed from the outside.

In addition, in the case it becomes necessary to replace the medium in the main culture vessel after a predetermined amount of time has elapsed, restriction on the flow of fluid through the connecting line between the main culture vessel and waste medium vessel is removed, and medium is allowed to flow from the main culture vessel towards the waste medium vessel. As a result, waste medium that is no longer required in the main culture vessel can be discharged into the waste medium vessel.

Subsequently, cell culturing is continued by again allowing medium to flow from the medium vessel towards the main culture vessel and restricting the flow of fluid in the connecting line.

In this manner, since cell culturing and the supply and replacement of medium required for cell culturing can be carried out in a vessel that is completely sealed, even if the culturing of numerous types of cells is carried out in extremely close proximity, intermixing of cells and contamination by bacteria and so forth can be inhibited.

In addition, the present invention provides a culture vessel in which the aforementioned connecting lines are provided with valves, and the flow of fluid within the connecting lines is allowed or restricted by said valves. According to this culture vessel, the flow of fluid in the connecting lines can be controlled by controlling the valves. As a result, the connecting lines can be opened and closed easily making it possible to switch between steps such as inflow of medium from the medium vessel to the main culture vessel, discharge of medium from the main culture vessel to the waste medium vessel and culturing of cells within the main culture vessel.

In addition, the present invention provides a culture vessel in which the connecting lines are made of a flexible material and the flow of fluid therein is restricted by clamping those connecting lines. According to this culture vessel, the flow of fluid is restricted as a result of the connecting lines made of a flexible material being crushed when they are pressed on from outside the culture vessel, thereby blocking the flow path inside. As a result, the constitution of the culture vessel can be simplified without providing valves in the connecting lines. The use of a simpler constitution to reduce costs is preferable in the case a disposable culture vessel is used for each batch of cells.

In addition, the present invention provides a culture vessel in which a blood collection line is connected to the main culture vessel. According to this culture vessel, by inserting the blood collection line into a patient and collecting blood, bone marrow or other body fluid from the patient, cells to be cultured can be supplied to the main culture vessel.

In addition, the present invention provides a culture vessel in which at least one enzyme vessel in which a protease enzyme is sealed is connected to the main culture vessel by a connecting line that restricts the flow of fluid between them in a state in which it is sealed from the outside. According to this culture vessel, in the case of, for example, culturing adhesive cells such as mesenchymal stem cells, cells grow by adhering to the inner wall of the main culture vessel after a predetermined culturing period has elapsed. Thus, in the case of collecting such cells, the cells can be detached from the inner wall of the main culture vessel by removing the restriction on flow in the connecting line between the enzyme vessel and main culture vessel and allowing protease enzyme to flow into the main culture vessel after having discharged the medium in the main culture vessel into the waste medium vessel.

In addition, the present invention provides a culture vessel in which a body tissue supplement material is sealed. According to this culture vessel, when cells are placed in the main culture vessel and medium is supplied to the main culture vessel, the cells adhere to the body tissue supplement material sealed within the main culture vessel, allowing the cells to grow by using the body tissue supplement material as a scaffold. By then repeating the supply of medium from the medium vessel to the main culture vessel and the discharge of unnecessary medium from the main culture vessel to the waste medium vessel during a suitable culturing period, a body tissue supplement can be produced in which cells have adequately grown on the body tissue supplement material.

In addition, the present invention provides a culture vessel in which a body tissue supplement material is sealed in the main culture vessel, and at least one type of growth accelerator vessel, in which a growth accelerator containing growth factor is sealed, is connected to the main culture vessel by a connecting line capable of restricting the flow of fluid between them in a state in which it is sealed from the outside. According to this culture vessel, the growth of cells can be accelerated during culturing by removing the restriction on the flow of fluid in the connecting line between the main culture vessel and growth accelerator vessel and allowing growth accelerator containing growth factor to flow into the main culture vessel.

In addition, the present invention provides a culture vessel in which the connecting lines are made of a material that can be sealed or fused by heat. According to this culture vessel, only the main culture vessel in particular can be separated from the other vessels by sealing the connecting lines with heat. Thus, for example, by separating only the main culture vessel by sealing the connecting lines with heat at completion of the culturing period, only the cells that have grown can be transported or delivered. In addition, in the case of culturing with a body tissue supplement material, by separating only the main culture vessel, only the body tissue supplement can be transported and delivered in a sealed form. In addition, as a result of composing the connecting lines with a material that can be fused by heat, cells can be transferred from one main culture vessel to another main culture vessel by fusing the corresponding connecting lines. In this case, since cell transfer can also be carried out in a space that is sealed from the outside, contamination by bacteria and so forth can be inhibited.

In addition, the present invention provides a culture vessel in which the main culture vessel is provided with an occluded connecting line, the end of which is occluded, and the occluded connecting line is made of a material that can be sealed or fused by heat. According to this culture vessel, two main culture vessels can be connected by severing and then fusing an occluded connecting line provided on one main culture vessel and an occluded connecting line provided on another main culture vessel with heat. For example, a body tissue supplement can be produced by passing cells adequately grown in one main culture vessel through an occluding connecting line and transferring them to another main culture vessel in which a body tissue supplement material is sealed.

In addition, the present invention preferably composes each of the vessels that compose the culture vessel to have a variable inner volume. According to this constitution, fluid can be transferred between vessels by reducing the inner volume of the vessel.

In addition, the present invention provides a culture apparatus provided with a culture vessel as claimed in the present invention, and a means for allowing a fluid within the vessels that compose the culture vessel to flow into the connecting lines provided in said vessels.

In the culture apparatus of the present invention, a constitution is preferably employed in which each vessel that composes the culture vessel has a variable inner volume, and the culture apparatus is provided with a case provided with indentations for housing each vessel that composes said culture vessel, and a pressing means that contracts each vessel housed in the indentations by applying external pressure. According to this culture apparatus, by housing each vessel of a culture vessel in which a plurality of vessels are connected with connecting lines in indentations formed in the case, the culture vessel is held in the case, thereby improving ease of handling by being able to be handled as a single unit. By allowing the pressing means to act in this state, each vessel is contracted by selectively applying external force. At this time, by removing the restrictions on flow of the connecting tubes connecting the contracted vessels, the fluid sealed inside the contacted vessels can be transferred to another vessel through the connecting lines. At this time, since each vessel is held in an indentation provided in the case, the fluid inside can be made to efficiently flow out simply by pressing the pressing means.

In addition, the present invention provides a culture apparatus in which the connecting lines are made of a flexible material, the flow of fluid within the connecting lines is restricted by clamping the lines, connecting line pathways are provided in the case through which the connecting lines of the culture vessel pass, and valve means are provided that restrict the flow of fluid through the connecting lines by clamping the connecting lines disposed in the connecting line pathways in the radial direction. According to this culture apparatus, as a result of housing each vessel that composes the culture vessel in indentations provided in the case, each vessel is integrally held in the case thereby improving handling ease. In this case, the connecting lines that connect each vessel are disposed so as to pass through the connecting line pathways provided in the case. Since valve means are disposed in the connecting line pathways, the connecting lines disposed in the case are crushed so as to block the flow path inside as a result of external force being applied in the radial direction by the valve means, thereby restricting the flow of fluid.

In addition, the present invention provides a culture apparatus provided with a centrifuge that rotates the case with the culture vessel inside, and the indentations that house the main culture vessels are disposed at intervals from the axis of rotation. According to this culture apparatus, as a result of the operation of the centrifuge rotating the case to which culture vessels are attached with the culture vessels still attached, medium and cells arranged inside the main culture vessels can be separated by centrifugation. Since the main culture vessels are disposed at intervals from the axis of rotation of the centrifuge, separated cells accumulate at a fixed location farthest away in the radial direction from the center of the axis of rotation.

In addition, the present invention provides a culture apparatus in which an occluded connecting line having an occluded end is provided on the main culture vessel, the occluded connecting line is made of a material that can be sealed or fused with heat, the case is provided with a centrifuge that rotates the case with reaction vessels inside, and the occluded connecting line is disposed outward in the radial direction of the main reaction vessel centered about the center of the axis of rotation in the state in which the main culture vessel is housed in indentations of the case. According to this culture apparatus, although separated cells accumulate at the location farthest away in the radial direction from the center of the axis of rotation, since occluded connecting lines are disposed at this location, the centrifuged cells can be efficiently removed to the outside from the occluded connecting lines when pushed out from the main culture vessel.

BEST MODE FOR CARRYING OUT THE INVENTION

FIRST EMBODIMENT

Culture Vessel

The following provides an explanation of a culture vessel as claimed in a first embodiment of the present invention with reference to the drawings.

Figure 1:
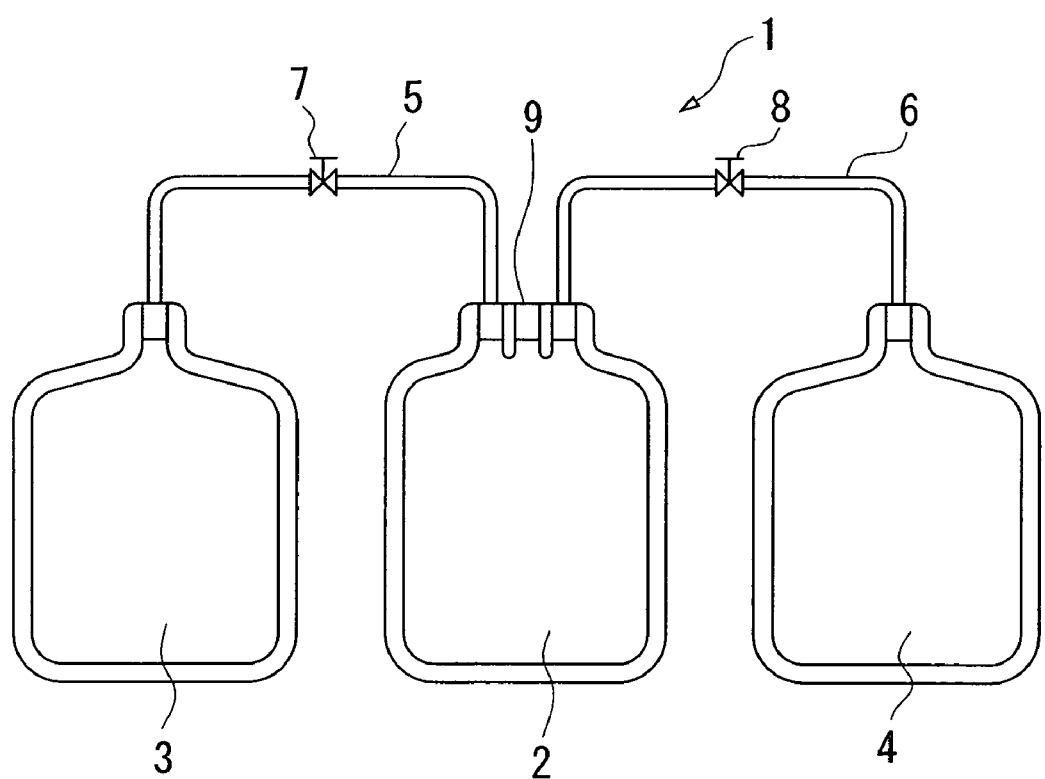
FIG. 1 is a front view showing a culture vessel as claimed in a first embodiment of the present invention.

As shown in FIG. 1, the culture vessel as claimed in the present embodiment is composed of one main culture vessel 2, one medium vessel 3, one waste medium vessel 4, a first connecting line 5 that connects main culture vessel 2 and medium vessel 3, and a second connecting line 6 that connects main culture vessel 2 and waste medium vessel 4.

Main culture vessel 2, medium vessel 3 and waste medium vessel 4 are respectively composed of a flexible material such as vinyl chloride. In addition, first and second connecting lines 5 and 6 are also composed of flexible tubes such as those made from vinyl chloride. Each of these vessels 2 through 4 and connecting lines 5 and 6 are able to mutually connect their internal spaces, and are connected in a state in which their inner space is sealed from the outside. Namely, valves 7 and 8 that can be opened and closed from the outside are provided at intermediate locations of first and second connecting lines 5 and 6.

In addition, a medium such as minimum essential medium (MEM), fetal bovine serum (FBS) and an antibiotic and so forth is sealed in the aforementioned medium vessel 3 adjusted to a predetermined blending ratio of, for example, 84:15:1. Human serum may be used instead of FBS. The aforementioned waste medium vessel 4 is initially empty and arranged in a sufficiently contracted state.

The aforementioned main culture vessel 2 is provided with an injection port 9 that can be penetrated with an injection needle and closes due to elasticity after the injection needle has been removed. As a result, a body fluid such as bone marrow fluid can be injected into the main culture vessel by puncturing the injection port with an injection needle of a syringe used to collect bone marrow fluid, and the inside of main culture vessel 2 can be isolated from the outside by retracting the injection needle from the injection port.

Figure 2:
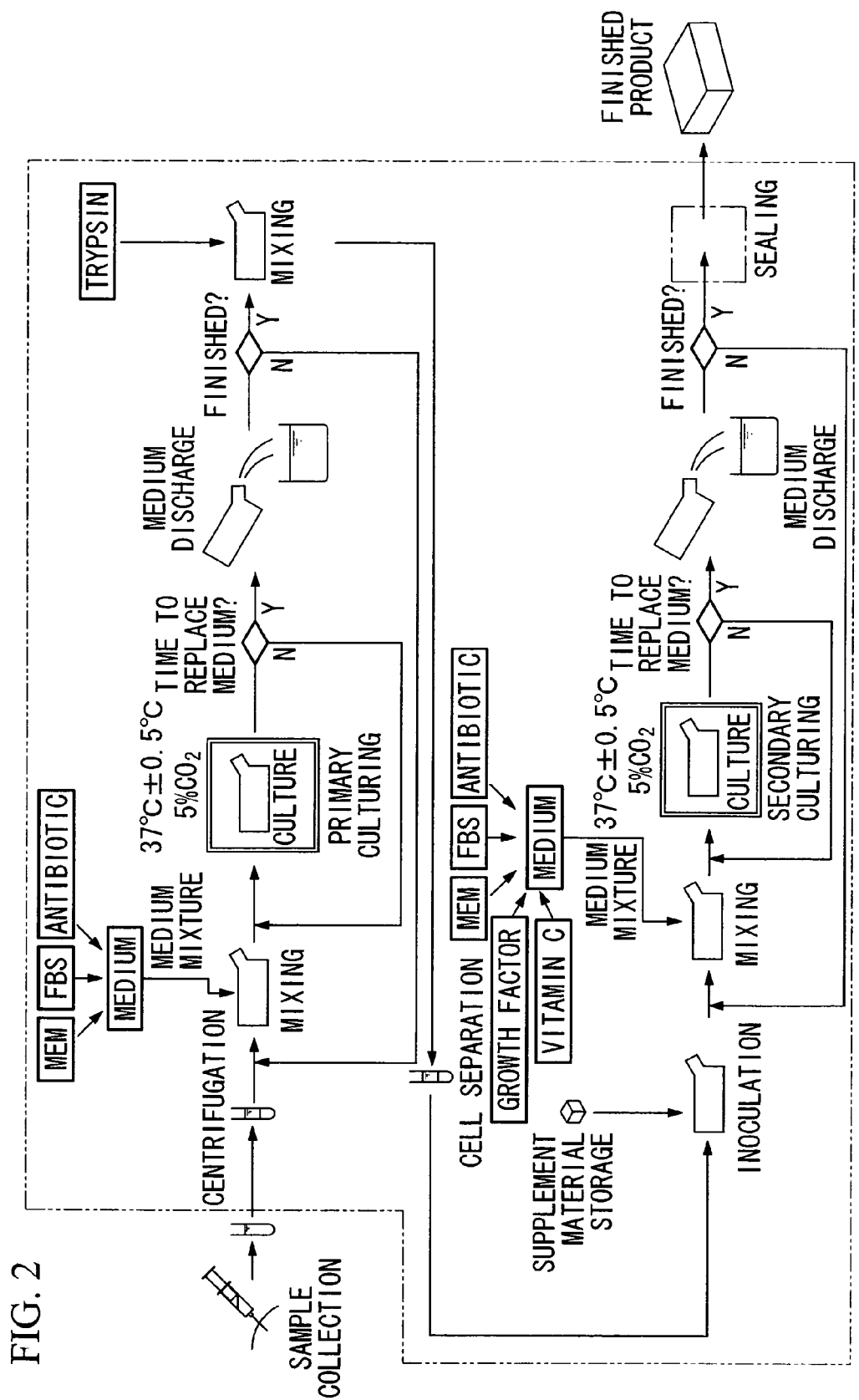
FIG. 2 is an explanatory drawing for explaining a culturing step that applies the present invention.

Prior to explaining the operation of culture vessel 1 as claimed in the present embodiment composed in this manner, a general explanation is provided of the production process of a bone supplement used as a body tissue supplement. As shown in FIG. 2, in order to produce a bone supplement, bone marrow fluid is first collected from the iliac bone and so forth of a patient. The collected bone marrow fluid is placed in a centrifuge and spun to extract the bone marrow cells having a larger specific gravity.

The extracted bone marrow cells are loaded into a culture vessel together with pre-prepared medium and mixed. A portion of the medium is removed and subjected to examination for infection.

Subsequently, the cells are subjected to primary culturing by culturing the mixed bone marrow fluid and medium under fixed culturing conditions for a predetermined amount of time by maintaining at culturing conditions such as a predetermined temperature (e.g., 37±0.5° C.), humidity (e.g., 100%) and $CO_2$ concentration (e.g., 5%). The medium is discarded from the culture vessel at predetermined replacement times during the course of cell culturing. Medium is then again mixed in and culturing is continued by repeating the culturing step. A portion of the discarded medium is subjected to examination for infection.

Following the completion of a predetermined culturing period, and after the medium is discarded from the culture vessel, a protease enzyme such as trypsin is added to the culture vessel and mixed. As a result, mesenchymal stem cells that have grown by adhering to the bottom of the culture vessel are detached from the bottom of the main culture vessel. The mesenchymal cells that have been detached in this manner are then extracted by spinning in a centrifuge.

After adjusting the number of cells, the extracted mesenchymal stem cells are mixed in a culture vessel containing a bone supplement material and a suitable medium. In actuality, the mesenchymal stem cells are loaded into the medium by adhering to the bone supplement material. The mixed mesenchymal stem cells and medium are then cultured under fixed culturing conditions over a predetermined amount of time by maintaining at culturing conditions such as a predetermined temperature (e.g., 37±0.5° C.), humidity (e.g., 100%) and $CO_2$ concentration (e.g., 5%) in the same manner as previously described to carry out secondary culturing.

In this secondary culturing step as well, the medium is periodically replaced in the same manner as in the primary culturing step, and a portion of the added medium and a portion of the discarded medium are respectively subjected to examinations for infection. After a predetermined culturing period has elapsed, specimens for quality testing for shipping and for infection examinations are extracted, and the produced bone supplement material is sealed and provided as a finished product.

The following provides an explanation of the operation of culture vessel 1 as claimed in the present embodiment. The culture vessel 1 as claimed in the present embodiment is the culture vessel 1 used in the primary culturing step among the culturing steps described above.

Figure 3:
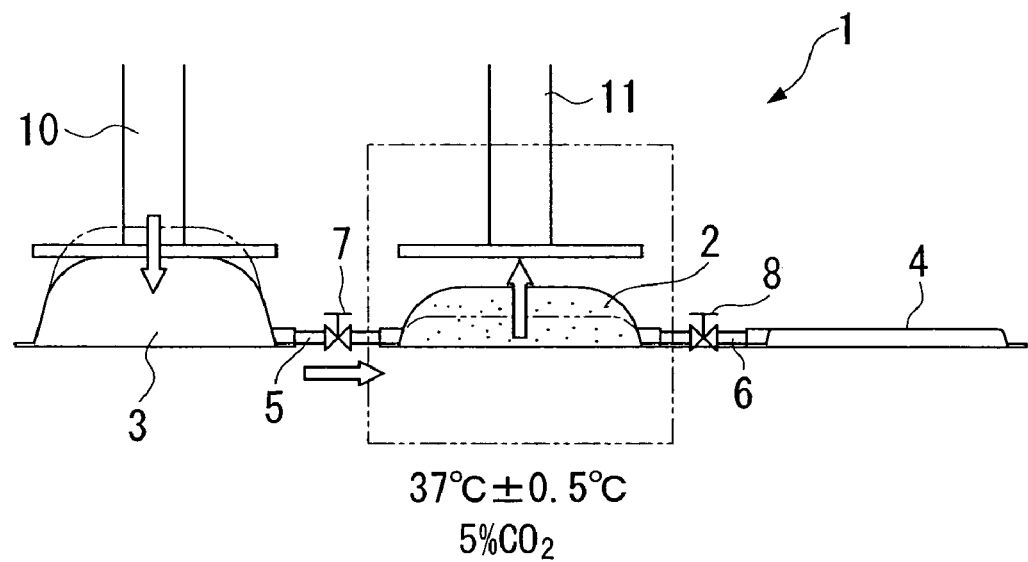
FIG. 3 is a schematic drawing for explaining a step in which medium is supplied from a medium vessel to a main culture vessel using the culture vessel of FIG. 1.

As was previously described, bone marrow fluid is injected into main culture vessel 2 by penetrating an injection port 9 with the injection needle of a syringe used to collect bone marrow fluid. Together with opening valve 7 provided in first connecting line 5, as shown in FIG. 3, the inner volume of medium vessel 3 is contracted by applying a force from the outside such as pressing by piston 10. As a result, a predetermined amount of medium is supplied from medium vessel 3 into main culture vessel 2, and mixed with the bone marrow fluid injected into main culture vessel 2. At this time, valve 8 provided in second connecting line 6 is closed.

Culturing is then carried out by then subjecting main culture vessel 2 to culturing conditions such as a temperature of 37±0.5° C. and $CO_2$ concentration of 5% while in this state. The $CO_2$ culturing conditions can be achieved by either dissolving $CO_2$ in the medium or composing all or a portion of main culture vessel 2 with a $CO_2$-permeable filter.

Figure 4:
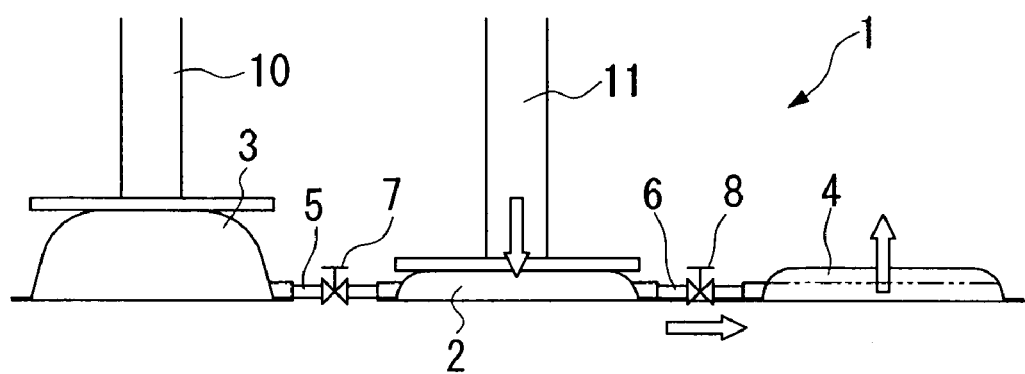
FIG. 4 is a schematic drawing similar to FIG. 3 for explaining a step in which medium is discharged from a main culture vessel to a waste medium vessel.

Subsequently, when a predetermined medium replacement time has been reached, as shown in FIG. 4, valve 8 provided in second connecting line 6 is opened and main culture vessel 2 is contracted by applying an external force such as a pressing force with piston 11. As a result, medium that is no longer necessary is discharged from main culture vessel 2 into waste medium vessel 4 through valve 8.

When a predetermined amount of medium has been discharged, valve provided in second connecting line 6 is again closed, valve 7 provided in first connecting line 5 is opened, and as shown in FIG. 3, medium vessel 3 is contracted. As a result, fresh medium is again supplied to main culture vessel 2.

Mesenchymal stem cells are then adequately grown by continuing culturing while repeating this medium replacement step. Main culture 2 that houses the grown mesenchymal stem cells can be transported separately by sealing all connecting lines 5 and 6 that are connected to said main culture vessel 2 and then severing those lines.

In this manner, according to culture vessel 1 as claimed in the present embodiment, medium and so forth required for culturing can be sealed in advance, and the contents of culture vessel 1 can be isolated from the outside in a sealed state throughout the culturing period of the primary culturing step. As a result, together with being able to prevent contamination by dust particles and bacteria from the outside, the effects of contamination and infection by other outside cells can also be eliminated. As a result, numerous types of cells can be cultured simultaneously in close proximity thereby improving culturing efficiency.

Furthermore, although culture vessel 1 as claimed in the present embodiment has been explained as being applicable to a primary culturing step in which mesenchymal stem cells are grown while replacing the medium a plurality of times at predetermined times, culture vessel 1 can also be composed so as to be applicable to a secondary culturing step in which a bone supplement material such as a β-tricalcium phosphate porous body is sealed in main culture vessel 2 so as to allow addition of mesenchymal stem cells cultured in a primary culturing step.

Figure 5:
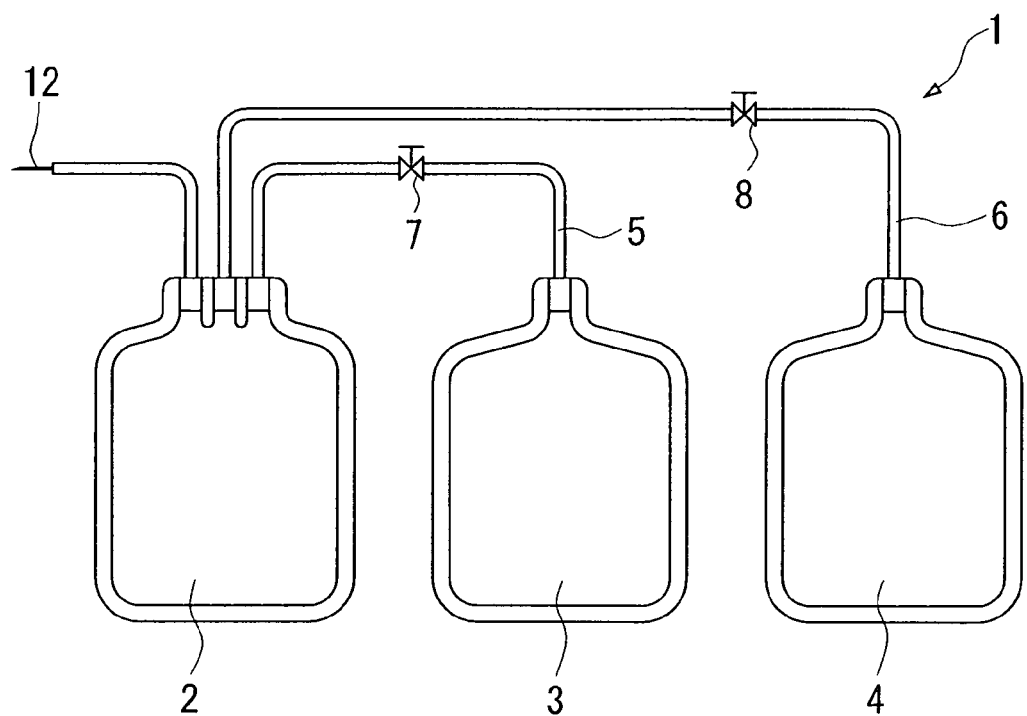
FIG. 5 is a front view showing a variation of the culture vessel of FIG. 1.

In addition, as shown in FIG. 5, a blood collection line 12 may be connected to main culture vessel 2, and bone marrow fluid collected from a patient can be added to main culture vessel 2 by said blood collection line 12.

Figure 6:
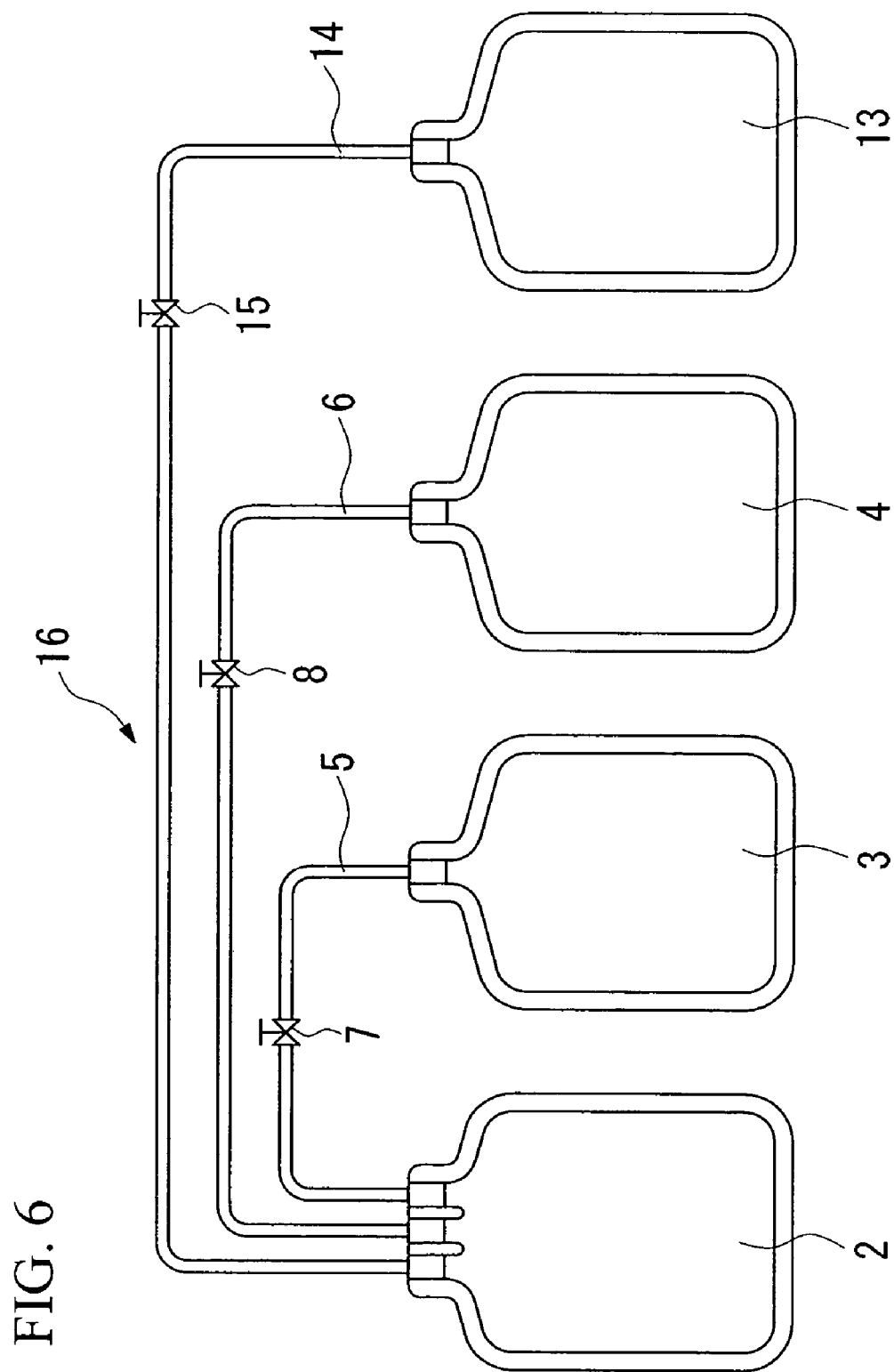
FIG. 6 is front view showing another variation of the culture vessel of FIG. 1.

In addition, as shown in FIG. 6, a variable inner volume enzyme vessel 13 may be connected to main culture vessel 2 by means of a third connecting line 14. A protease enzyme such as trypsin, for example, is loaded into enzyme vessel 13, and a valve 15 is provided in third connecting line 14.

According to a culture vessel 16 composed in this manner, following completion of a primary culturing step in which mesenchymal stem cells have grown by adhering to the inner walls of main culture vessel 2, valve 8 provided in second connecting line 6 is opened and medium that is no longer necessary is discharged from inside main culture vessel 2 to waste medium vessel 4 through valve 8. After then closing valve 8 of second connecting line 6, valve 15 in third connecting line 14 is opened and trypsin is supplied to main culture vessel 2. As a result, mesenchymal stem cells are detached from the inner walls of main culture vessel 2 and can then be collected.

Furthermore, temperature-responsive treatment switching between hydrophilic and hydrophobic properties bordering on a predetermined temperature may also be carried out on the inner walls of main culture vessel 2 without using trypsin or other protease enzyme.

Temperature-responsive treatment is carried out by immobilizing the temperature-responsive polymer poly(N-isopropylacrylamide) on the inner walls by covalent bonding. Although the region subjected to temperature-responsive treatment exhibits weak hydrophobic properties to the same degree as commercially available cell culture vessels at temperatures equal to or above a boundary temperature of 32° C., this region exhibits highly hydrophilic properties by cooling the temperature to equal to or below the boundary temperature. Thus, by culturing at 37° C. followed by cooling to 32° C. or below, for example, the inner walls of main culture vessel 2 are changed so as to exhibit highly hydrophilic properties, thereby enabling non-invasive detachment of mesenchymal stem cells.

Figure 7:
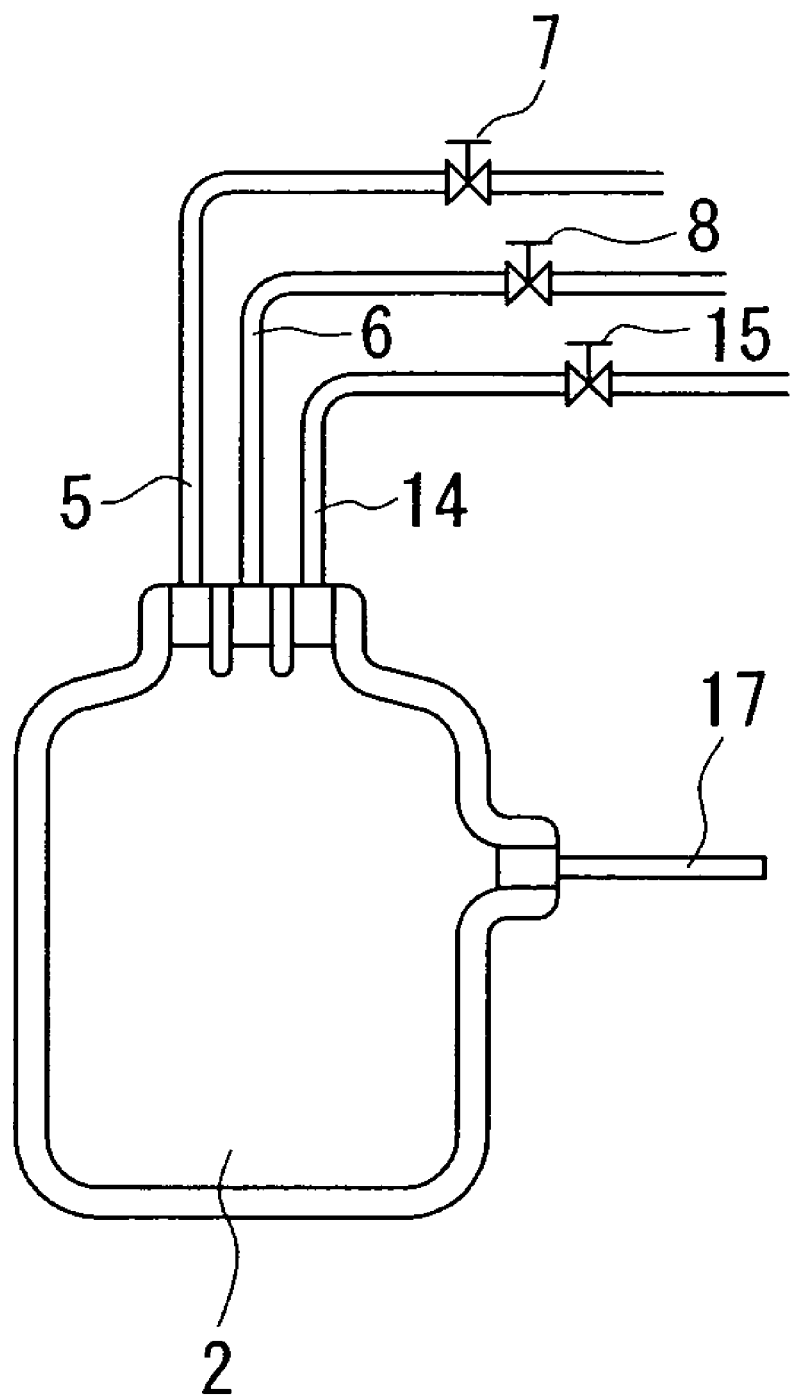
FIG. 7 is a front view showing another variation of the culture vessel of FIG. 1.

In addition, as shown in FIG. 7, main culture vessel 20 may also be provided with an occluded connecting line 17 having an occluded end. This occluded connecting line 17 is composed of a material such as vinyl chloride that can be sealed or fused by heat.

Figure 8A:
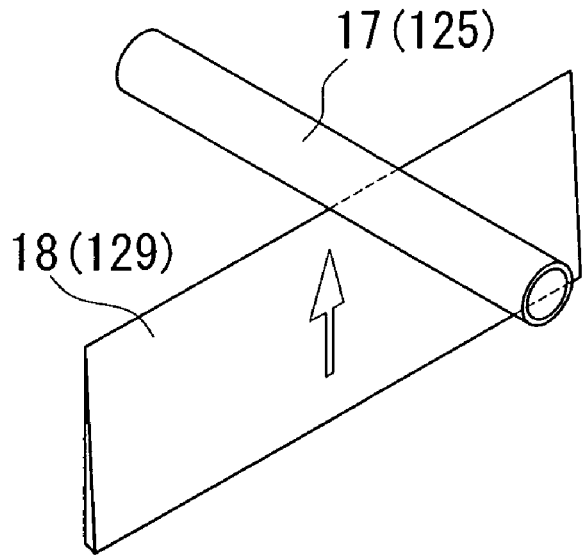
FIGS. 8A, 8B and 8C are perspective views for explaining the order of steps for aseptically severing a tube.
Figure 8B:
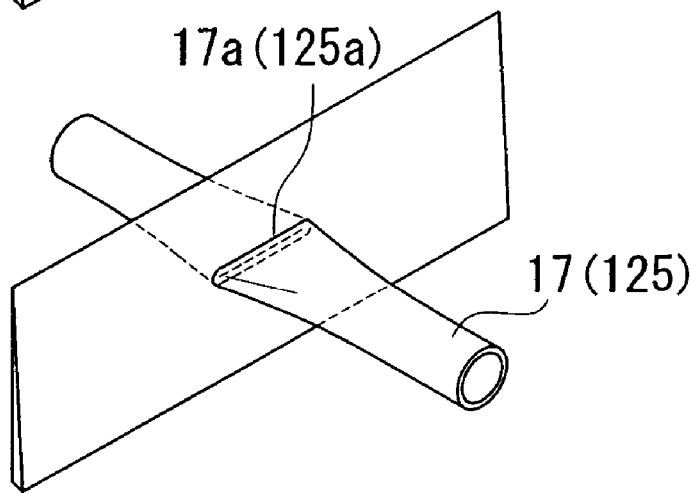
Figure 8C:
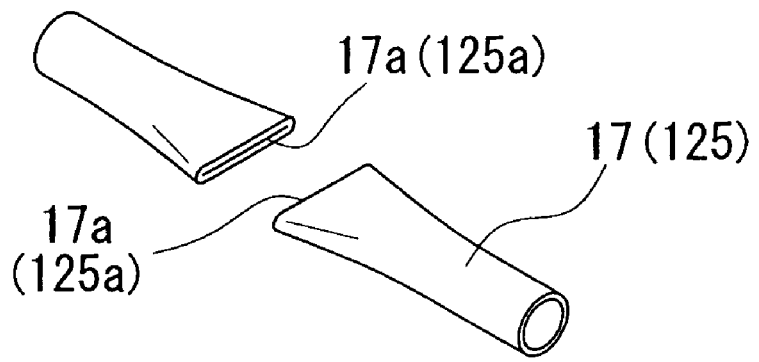

An occluded connecting line 17 composed in this manner can be obtained by using a heating plate 18 that moves in the direction of shearing as shown in FIG. 8A, severing while melting the connecting line as shown in FIG. 8B, and occluding the severed end while maintaining the inside of the connecting tube in a sterile and sealed state as shown in FIG. 8C. This severing procedure is referred to as aseptic tube severing.

Figure 9A:
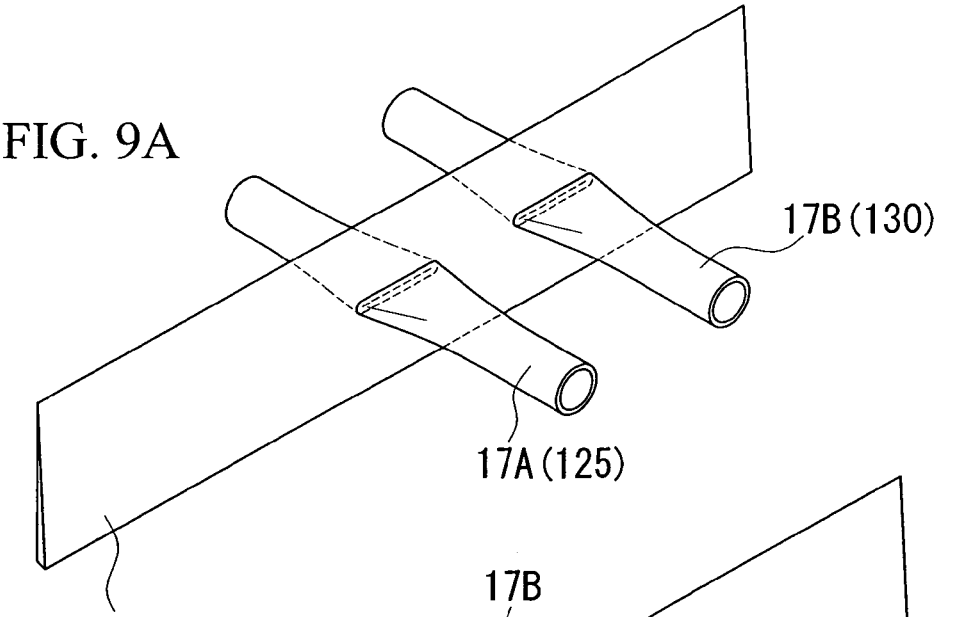
FIGS. 9A, 9B and 9C are perspective views for explaining the order of steps for aseptically connecting a tube.
Figure 9B:
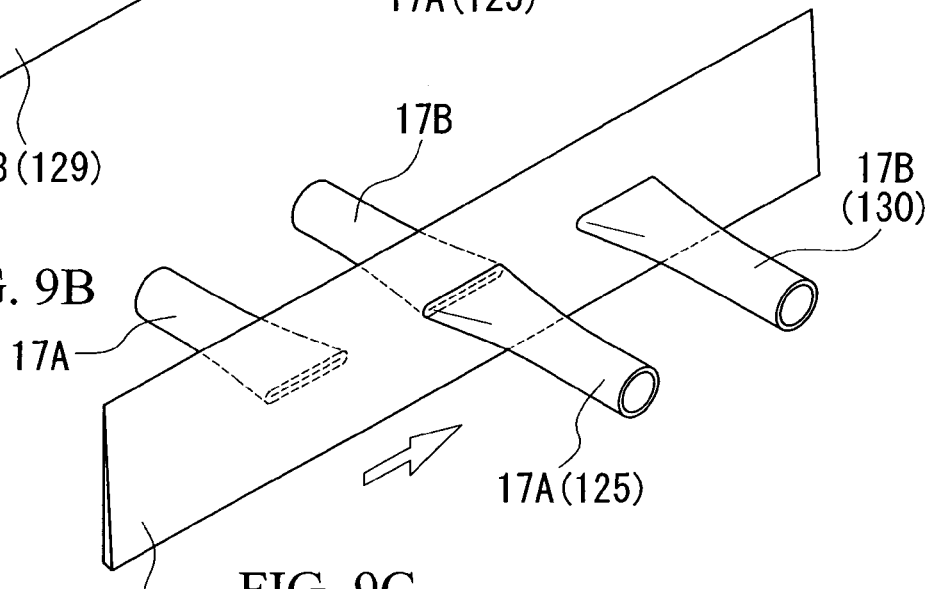
Figure 9C:
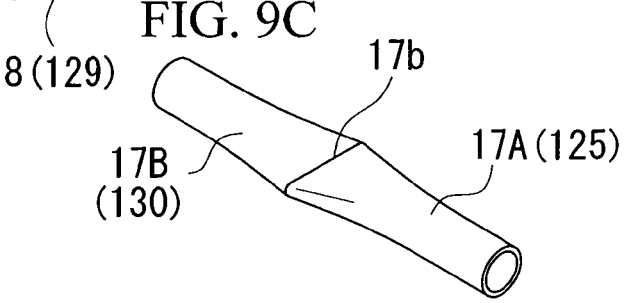

In addition, after simultaneously severing two occluded connecting lines 17A and 17B arranged in parallel as shown in FIG. 9A, and shifting the lines so that one connecting tube 17A aligns with the other connecting line 17B as shown in FIG. 9B, the one connecting line 17A is connected to the other connecting line 17B by removing heating plate 18 as shown in FIG. 9C. Although the joined portion 17b is occluded during connection, the internal flow path is able to be continuous while the line walls are connected by an external force. Namely, different connecting lines 17A and 17B can be connected while maintaining the inside in a sterile state. This connection procedure is referred to as aseptic tube connection.

Namely, by providing this type of occluded connecting line 17, cells can be transferred to another main culture vessel 2 by connecting a first main culture vessel 2 in which cells have been cultured to another main culture vessel 2 using aseptic tube connection. A primary culturing step and a secondary culturing step can then be linked by using the first main culture vessel 2 as the primary culture vessel and another main culture vessel 2 as a secondary culture vessel.

Figure 10:
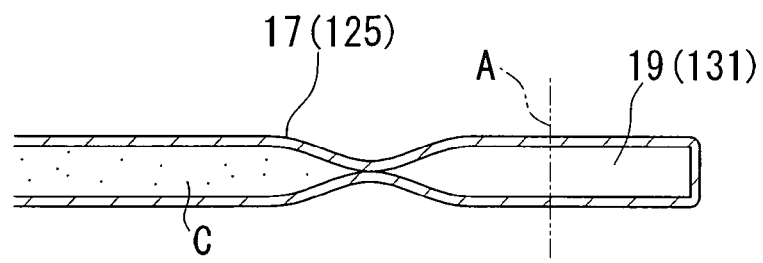
FIG. 10 is a longitudinal cross-sectional view showing the end structure of an occluded connecting tube.

Furthermore, in the case cells C are present in occluded connecting line 17, since there is the risk of the cells C being damaged by heating plate 18, as shown in FIG. 10, a spare space 19 for severing may be formed in the end of occluded connecting line 17. Namely, by severing along cross-sectional line A that passes through spare space 19, heating plate 18 is prevented from making direct contact with cells C in occluded connecting line 17, thereby making it possible to carry out aseptic tube connection while maintaining the viability of cells C.

SECOND EMBODIMENT

Culture Apparatus

Next, an explanation is provided of a culture apparatus as claimed in an embodiment of the present invention with reference to the drawings.

Figure 11:
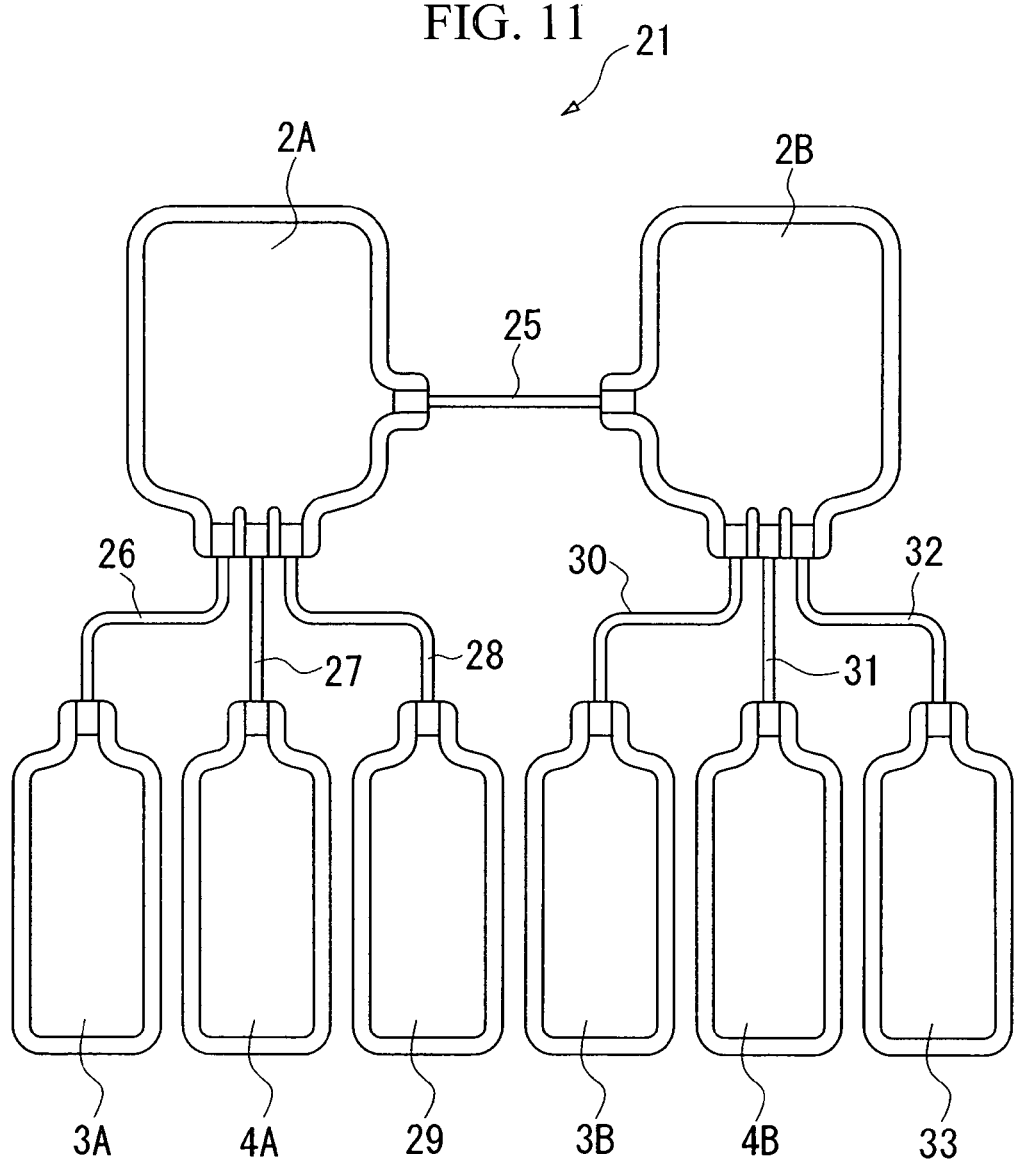
FIG. 11 is a front view showing culture vessels used in a culture apparatus as claimed in a second embodiment of the present invention.
Figure 12:
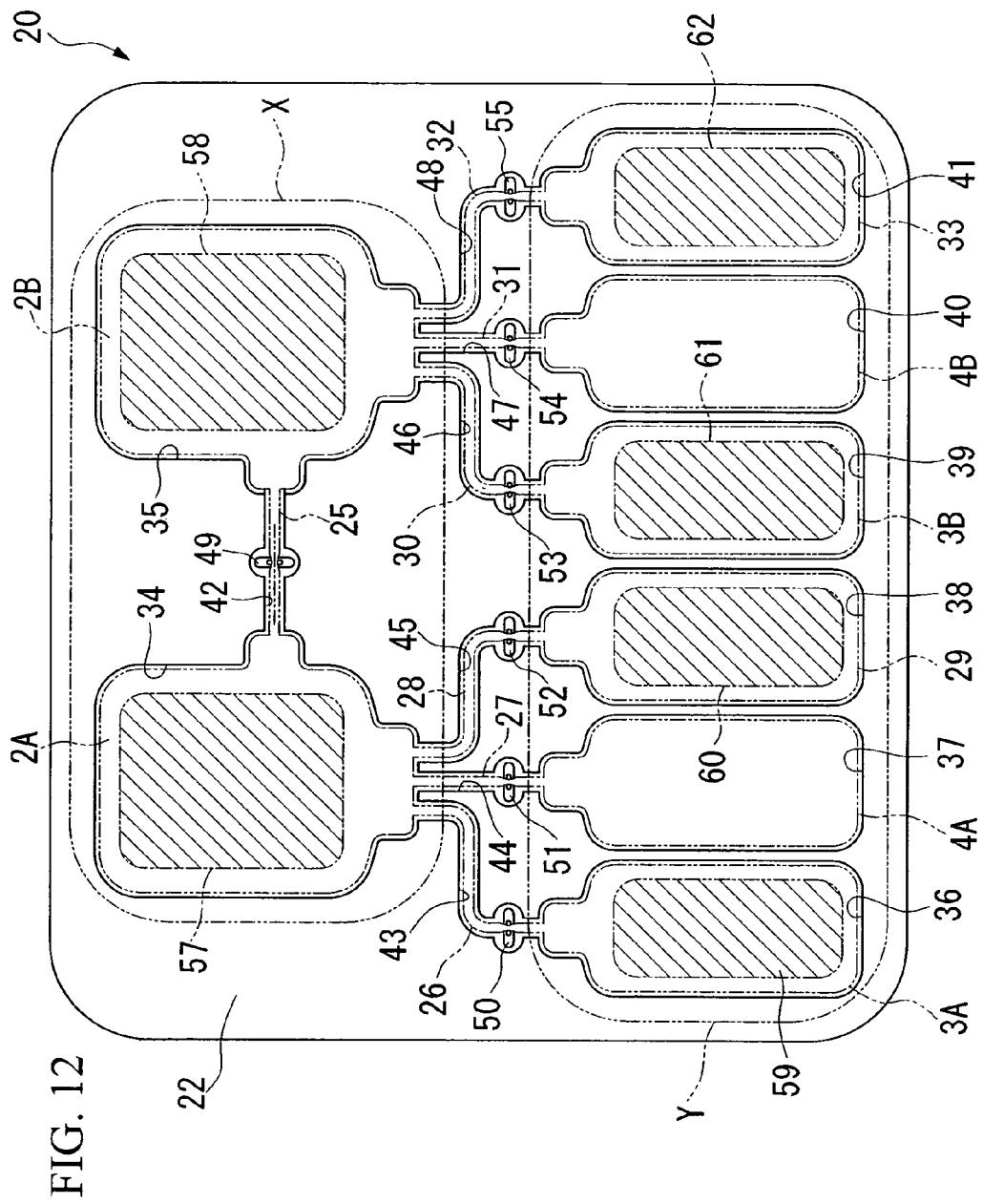
FIG. 12 is an overhead view showing a case in which the culture vessels of FIG. 11 are housed.
Figure 13:
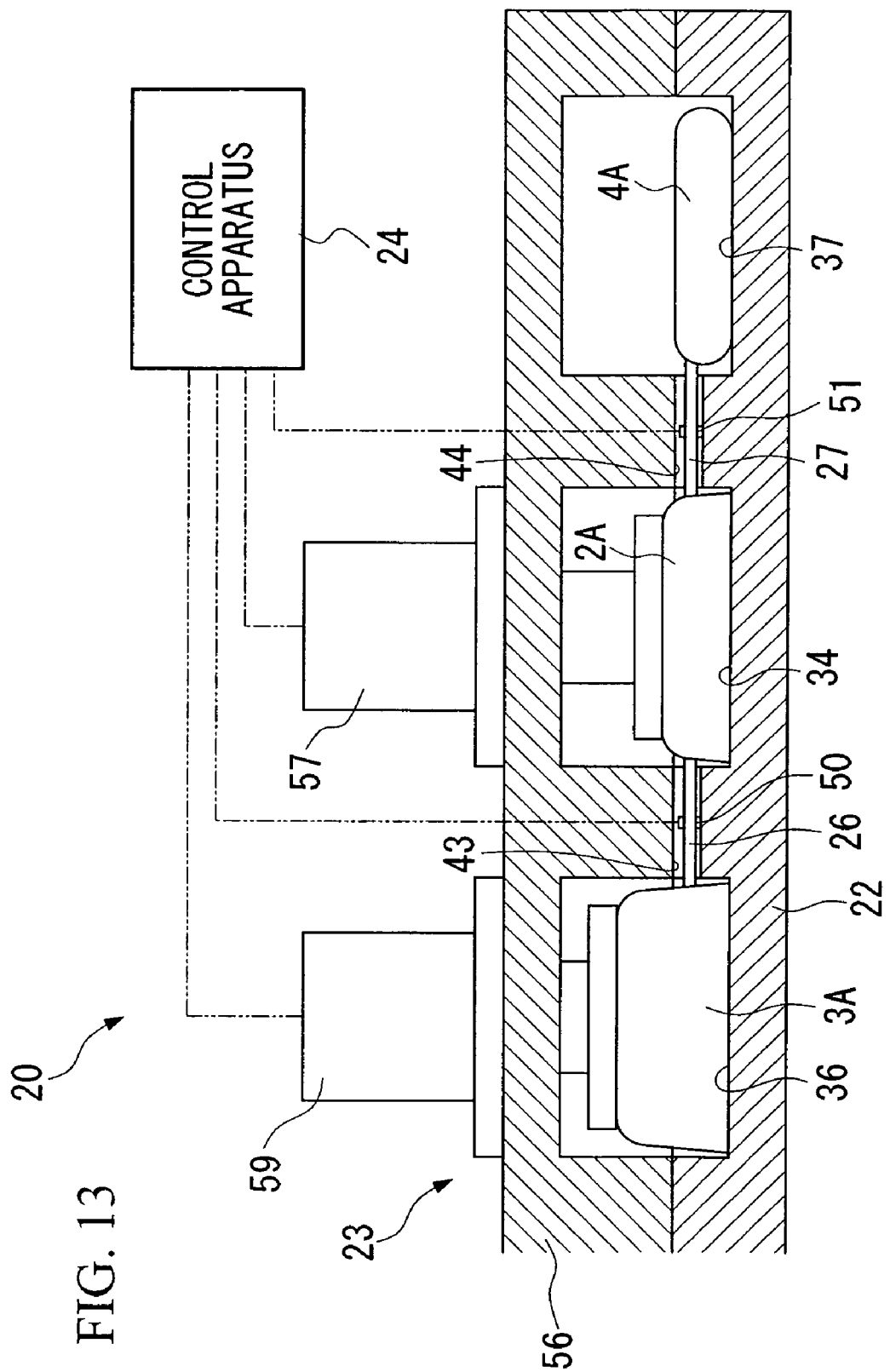
FIG. 13 is a longitudinal cross-sectional view showing the culture apparatus of FIG. 11 partially severed.

As shown in FIGS. 11 through 13, culture apparatus 20 as claimed in the present embodiment is provided with a culture vessel 21, a case 22 in which it is housed, a pressing apparatus that presses on culture vessel 21, and a control apparatus 24 that controls these operations.

As shown in FIG. 11, culture vessel 21 is provided with two main culture vessels 2A and 2B that are mutually connected by a first connecting line 25, a first medium vessel 3A, a fist waste medium vessel 4A and an enzyme vessel 29 connected to a first main culture vessel 2A by second through fourth connecting lines 26 through 28, and a second medium vessel 3B, a second waste medium vessel 4B and a growth accelerator vessel 33 connected to a second main culture vessel 2B by fifth through seventh connecting lines 30 through 32.

Each of these vessels 2A, 2B, 3A, 3B, 4A, 4B, 29 and 33 are thin-walled vessels made of vinyl chloride in the same manner as each of vessels 2, 3 and 4 of culture vessel 1 as claimed in the first embodiment, and are composed to have a variable inner volume when pressed by an external force. A bone supplement material such as a β-tricalcium phosphate porous body is sealed within the second main culture vessel 2B. Medium, a protease enzyme such as trypsin and a growth factor such as dexamethasone similar to the first embodiment are respectively sealed in medium vessels 3A and 3B, enzyme vessel 29 and growth accelerator vessel 33.

In addition, first through seventh connecting lines 25 through 28 and 30 through 32 are each composed of a flexible material such as vinyl chloride. As a result, together with each vessel 2A, 2B, 3A, 3B, 4A, 4B, 29 and 33 being able to be arranged at an arbitrary position by bending each connecting line 25 through 28 and 30 through 32, the flow of liquid therein can be restricted by clamping connecting lines 25 through 28 and 30 through 32 with a clip or pinching valve in the radial direction at an intermediate location in the lengthwise direction thereof. Furthermore, in the state prior to first through seventh connecting lines 25 through 28 and 30 through 32 being attached to case 22, said connecting lines are occluded by a film, for example, that is ruptured by external force (not shown), to restrict the flow of fluid.

As shown in FIG. 12, the aforementioned case 22 is provided with a plurality of indentations 34 through 41 capable of respectively housing each vessel 2A, 2B, 3A, 3B, 4A, 4B, 29 and 33 that compose the aforementioned culture vessel 21 in an upper surface formed to have the shape of a flat plate. These indentations 34 through 41 are formed to dimensions of a degree to which each vessel 2A, 2B, 3A, 3B, 4A, 4B, 29 and 33 is held without shifting position as a result of indentations 34 through 41 housing each vessel 2A, 2B, 3A, 3B, 4A, 4B, 29 and 33.

Housing grooves 42 through 48 are formed between each indentation 34 through 41 that house each connecting line 25 through 28 and 30 through 32 connecting vessels 2A, 2B, 3A, 3B, 4A, 4B, 29 and 33. In addition, pinching valves 49 through 55 are arranged in each housing groove 42 through 48 that are able to clamp connecting lines 25 through 28 and 30 through 32 arranged in housing grooves 42 through 48 in the direction of diameter at an intermediate position in the direction of length of said housing grooves 42 through 48.

In addition, the aforementioned case 22 is divided by an insulating material (not shown) into a first area X, which contains indentations 34 and 35 that house the two main culture vessels 2A and 2B, and a second area Y, which contains indentations 36 through 41 that house the remaining vessels 3A, 3B, 4A, 4B, 29 and 33. The first area X can be maintained at a temperature of 37±0.5° C. suitable for culturing, and the periphery of main culture vessels 2A and 2B can be maintained in an atmosphere having a $CO_2$ concentration of 5%. In addition, the second area Y can be maintained in a cooled state at about, for example, 4° C.

As shown in FIG. 13, the aforementioned pressing apparatus 23 is provided with an apparatus body 56 that is placed on the upper surface of the aforementioned case 22, and pistons 57 through 62. Pistons 57 through 62 are provided at locations corresponding to each indentation 34 through 41 of case 22, and are composed so as to be able to be lowered and raised to a desired height. When pistons 57 through 62 are lowered, vessels 2A, 2B, 3A, 3B, 29 and 33 housed in indentations 34 through 36, 38, 39 and 41 arranged below are pressed and as a result, vessels 2A, 2B, 3A, 3B, 29 and 33 are contracted allowing the fluid inside to be pressed out from vessels 2A, 2B, 3A, 3B, 29 and 33.

The following provides an explanation of the operation of culture apparatus 20 as claimed in the present embodiment composed in this manner.

In order to culture cells C with the culture apparatus 20 as claimed in the present embodiment, control apparatus 24 is first operated to restrict the flow of fluid by clamping connecting lines 25 through 28 and 30 through 32 by closing all pinching valves 49 through 55. While in this state, patient bone marrow fluid is collected by a blood collection line or syringe not shown and loaded into first main culture vessel 2A.

Next, control apparatus 24 is operated to open pinching valve 50 that had been closing second connecting line 26 and then operate pressing apparatus 26 to lower piston 59 arranged above first medium vessel 3A and supply medium in first medium vessel 3A to first main culture vessel 2A through second connecting line 26. Subsequently, first main culture vessel 2A is sealed from the outside by again closing pinching valve 50 of second connecting line 26.

Since first main culture vessel 2A is arranged in first area X, it is subjected to predetermined culturing conditions. By allowing to stand for a predetermined amount of time in this state, cells C within first main culture vessel 2A grow in the medium by adhering to the bottom of main culture vessel 2A.

After a predetermined culturing period has elapsed, control apparatus 24 is operated to open pinching valve 51 that had been closing third connecting line 27, and lower piston 57 arranged above first main culture vessel 2A. As a result, the medium within first main culture vessel 2A is discharged into first waste medium vessel 4A. In this case, all of the medium in first main culture vessel 2A may be discharged or only a portion may be discharged. At this time, since cells C are maintained in an adhered state to the inner walls of first main culture vessel 2A, they remain within first main culture vessel 2A without flowing out to first waste medium vessel 4A.

Subsequently, pinching valve 51 of third connecting line 27 is again closed, and pinching valve 50 that had been closing second connecting line 26 is operated and opened. Simultaneous to this, piston 57 that had been pressing on first main culture vessel 2A from above is raised, and piston 59 arranged above first medium vessel 3A is lowered. As a result, medium in first medium vessel 3A is supplied to first main culture vessel 2A resulting in replacement of the medium inside first main culture vessel 2A.

After periodically repeating this medium replacement step a plurality of times, all or a portion of the medium in first main culture vessel 2A is discharged to first waste medium vessel 4A, and in the state in which pinching valve 51 of third connecting line 27 is closed, pinching valve 52 that had been closing fourth connecting line 28 is opened. Accompanying this, piston 57 above first main culture vessel 2A is raised up while lowering piston 60 arranged over enzyme vessel 29. As a result, the trypsin within enzyme vessel 29 is supplied to first main culture vessel 2A, and the cells C that had been growing by adhering to the inner walls of first main culture vessel 2A are detached from the inner walls.

Next, the entire culture vessel 21 is centrifuged while still in case 22 in the state in which the pinching valves of first through fourth connecting lines 25 through 28 connecting to first main culture vessel 2A are all closed. As a result, cells C in first main culture vessel 2A are separated from the medium and trypsin. When placing culture vessel 21 in the centrifuge, it is convenient to place culture vessel 21 so that first connecting line 25 that connects first main culture vessel 2A and second main culture vessel 2B is arranged outwardly in the radial direction when viewed from the centrifugal axis with respect to first main culture vessel 2A since the separated cells C collect in first connecting line 25.

After having been separated in this manner, cells C are transferred to second main culture vessel 2B through first connecting line 25 by opening pinching valve 49 arranged in first connecting line 25 and lowering piston 57 arranged above first main culture vessel 2A. Medium is then supplied to second main culture vessel 2B by opening pinching valve 53 of fifth connecting line 30 connected to second main culture vessel 2B and lowering piston 61 located above second medium vessel 3B. In addition, simultaneous or subsequent to this, dexamethasone or other growth factor is supplied to second main culture vessel 2B by opening pinching valve 55 of seventh connecting line 32 and lowering piston 62 located above growth accelerator vessel 33.

Since a bone supplement material is sealed within second main culture vessel 2B, cells C supplied from first main culture vessel 2A, medium supplied from second medium vessel 3B and growth factor supplied from growth accelerator vessel 33 are mixed therein. Since second main culture vessel 2B is arranged in first region X maintained at predetermined culturing conditions, secondary culturing is carried out by maintaining this state. During the secondary culturing period, medium replacement is carried out a plurality of times by periodically controlling the opening and closing of pinching valves 53 through 55 provided in fifth through seventh connecting lines 30 through 32, and the raising and lowering of pistons 58 through 62 arranged above second main culture vessel 2B, second medium vessel 3B and growth accelerator vessel 33. After a predetermined secondary culturing period has elapsed, a bone supplement is produced within second main culture vessel 2B by growing cells C using the bone supplement material as a scaffold.

The medium inside second main culture vessel 2B is then discharged into second waste medium vessel 4B by opening pinching valve 54 provided in sixth connecting line 47 and pressing on second main culture vessel 2B with piston 58. In this case, only a portion of the medium may be discharged. The bone supplement is then sealed in second main culture vessel 2B by closing pinching valves 49 and 53 through 55 of all connecting lines 25 and 30 through 32 connected to second main culture vessel 2B while in this state. The bone supplement can be shipped independently as a finished product by severing all connecting lines 25 and 30 through 32 while in the occluded state using, for example, aseptic tube severing, to separate the second main culture vessel 2B in which the bone supplement is sealed from the other vessels 2A, 3A, 3B, 4A, 4B, 29 and 33.

According to a culture apparatus 20 as claimed in the present embodiment composed in this manner, culturing can be carried out in a closed system that is completely isolated from the outside during the time from blood collection from a patient to completion of secondary culturing. Thus, contamination by dust particles and so forth from the outside can be prevented. Namely, cells can be maintained in a viable state by preventing contamination by dust particles from the outside in each of the transport, handling and culturing steps.

In addition, since culturing is carried out by arranging culture vessel 21 in case 22 having indentations 34 through 41, culture vessel 21 can be easily placed in culture apparatus 20. Thus, cells C can be cultured easily even by an operator unfamiliar with the apparatus. Moreover, different cells can be easily cultured in succession by replacing culture vessel 21 in which is sealed all the medium and other required substances.

In the aforementioned embodiment, since the media used in the primary and secondary culturing steps is stored in first and second waste medium vessels 4A and 4B, infection examinations and so forth may be carried out at each stage by using the media stored in these vessels 4A and 4B. In this case, first and second waste medium vessels 4A and 4B may be respectively and independently sent to an inspection step by severing third and sixth connecting lines 27 and 31 by aseptic tube severing. In addition, separate specimen extraction vessels not shown may be connected to first and second main culture vessels 2A and 2B. In addition, medium remaining in first connecting line 25 may also be used for examination.

In this manner, each vessel 2A, 2B, 3A, 3B, 4A, 4B, 29 and 33 can be separated by carrying out aseptic tube severing on first through seventh connecting lines 25 through 28 and 30 through 32 in the present embodiment. Symbols, and particularly bar codes, which indicate that the vessels are mutually related vessels, may be affixed to each vessel 2A, 2B, 3A, 3B, 4A, 4B, 29 and 33 to prevent the relationship between the cultured cells C, the discarded medium and so forth from becoming unclear as a result of the aforementioned separation. The bar codes may be identical bar codes or mutually correlated bar codes.

Furthermore, although the second main culture vessel 2B has been explained as being linked to the first main culture vessel 2A by means of first connecting line 25 from the outset in the aforementioned embodiment, second main culture vessel 2B may alternatively be connected to first main culture vessel 2A, second medium vessel 3B or second waste medium vessel 4B and so forth by aseptic tube connection. When this is done, a second main culture vessel 2B containing a bone supplement material corresponding to the amount and shape of the bone supplement desired to be produced can be suitably selected for use. In addition to porous blocks, granular, gel-like or other arbitrary forms of bone supplement materials can be made available for the bone supplement material sealed inside. In addition, an arbitrary biocompatible material can be used for the material.

In addition, a portion or all of first and second main culture vessels 2A and 2B may be composed to be transparent, and observation windows (not shown) may be formed in indentations 34 and 35 of case 22 that house these main culture vessels 2A and 2B. According to this, culturing status can be observed with, for example, an inverted microscope through an observation window during the culturing period.

In addition, although the finally produced bone supplement is loaded into an injection gun for injection into a patient's body, in order to carry this out in a sealed state, the injection gun (not shown) may be connected in advance by a connecting line (not shown) to second main culture vessel 2B. In addition, an injection gun may be subsequently connected to second main culture vessel 2B by aseptic tube connection. In addition, an injection gun capable may be made available that is capable of loading second main culture vessel 2B directly after separating from the other vessels 2A, 3A, 4A and 33 by aseptic tube severing, and a composition may be employed in which second main culture vessel 2B is ruptured within the injection gun allowing the bone supplement inside to be injected aseptically.

In addition, a porous bone supplement material may be arranged at the inlet to sixth connecting line 31 in second main culture vessel 2B. As a result, cells C suspended in medium discharged to second waste medium vessel 4B can be captured on the porous bone supplement material when discharged together with the medium. Thus, cells C can be recovered without waste. In addition to a β-tricalcium phosphate porous body, any arbitrary biocompatible material such as an apatite sheet can be used for the porous bone supplement material.

Moreover, when opening first through seventh connecting lines 25 through 28 and 30 through 32 with pinching valves 49 through 55 provided at intermediate locations in connecting lines 25 through 28 and 30 through 32, check valves (not shown), which allow the fluid therein to only flow in a desired direction of flow while prohibiting flow in the opposite direction, may be provided at intermediate locations in each of the connecting lines 25 through 28 and 30 through 32.

THIRD EMBODIMENT

Culture Apparatus

Next, an explanation is provided of a culture apparatus 70 as claimed in a third embodiment of the present invention with reference to the drawings. Furthermore, the same reference symbols are used for those locations in the present embodiment that are the same as the constitutions of each of the aforementioned embodiments, and their explanations are omitted.

Figure 14:
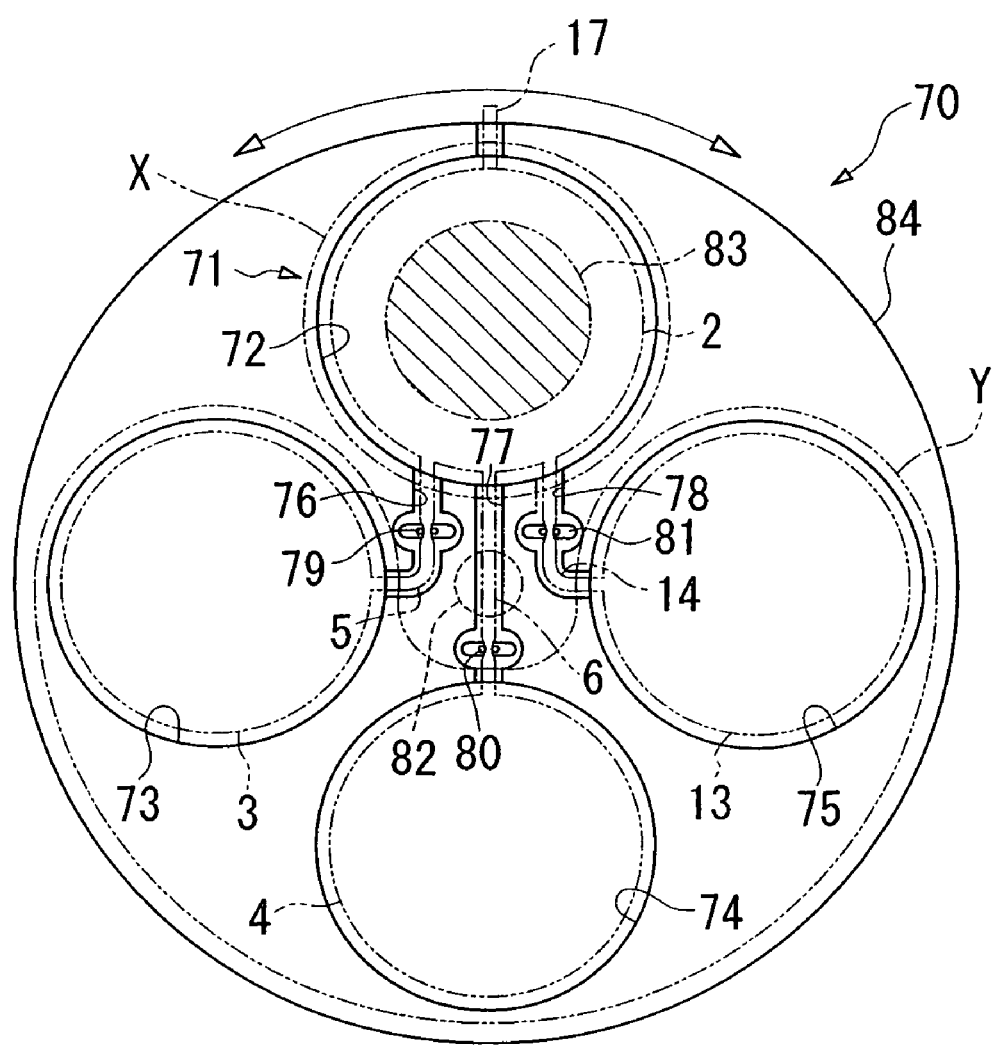
FIG. 14 is an overhead view showing a culture apparatus as claimed in a third embodiment of the present invention.

As shown in FIG. 14, culture apparatus 70 as claimed in the present embodiment is a culture apparatus 70 for carrying out a primary culturing step, and is provided with a culture vessel 71 composed by connecting a main culture vessel 2, a medium vessel 3 and a waste medium vessel 4 with connecting lines 5, 6 and 14, a case 84, a pressing apparatus (now shown) arranged above case 84, and a control apparatus for controlling them. Case 84 is provided with indentations 72 through 78 that house vessels 2 through 4 and 13 and connecting lines 5, 6 and 14.

Case 84 is formed in the shape of a disc, and is composed so as to be able to be rotated horizontally about vertical axial center 82 that passes through its center by the operation of a rotary drive mechanism not shown.

In addition, each vessel 2 through 4 and 13 is the same as the second embodiment with respect to being composed of a flexible material capable of changing volume, connecting lines 5, 6 and 14 are the same as the second embodiment with respect to being composed of a flexible material capable of closing the flow path inside as a result of being clamped in the radial direction, and pinching valves 79 through 81 that open and close connecting lines 5, 6 and 14 are the same as the second embodiment with respect to being provided in case 84. In addition, a first region X is maintained at a temperature of 37±0.5° C. and a second region Y is maintained at a temperature of 4° C. in the same manner as the second embodiment by a suitable heating means and cooling means.

In culture apparatus 70 as claimed in the present embodiment, indentations 72 through 78 that house each vessel 2 through 4 and 13, and particularly indentation 72 that houses main culture vessel 2 used to culture cells C, are arranged in a location away from the axial center of rotation. As a result, when case 84 is rotated about axial center of rotation 82, centrifugal force acts towards the outside in the radial direction on fluid inside main culture vessel 2 housed in indentation 72. Furthermore, indentations 73 through 75 that house the other vessels 3, 4 and 13 are also arranged at locations away from axial center of rotation 82 by the nearly same distance as indentation 72 housing main culture vessel 2.

In addition, culture vessel 71 of culture apparatus 70 as claimed in the present embodiment is provided with an occluded connecting line 17 connected to main culture vessel 2. This occluded connecting line 17 is made of vinyl chloride, and the end of which is occluded to prevent leakage of fluid inside. As shown in the drawing, this occluded connecting line 17 is arranged to the outside in the radiating direction of main culture vessel 2 as viewed from axial center of rotation 82 of case 84.

In addition, the aforementioned pressing apparatus is installed, for example, at the location indicated with broken lines in FIG. 14, and is provided with a single piston 83 that is moved up and down. Piston 83 is able to press on main culture vessel 2, medium vessel 3 and waste medium vessel 4, respectively, as a result of case 84 being rotated about axial center of rotation 82.

The following provides an explanation of the operation of culture apparatus 70 as claimed in the present embodiment composed in this manner.

The control apparatus is operated with cells C collected from a patient loaded in main culture vessel 2 to activate the rotary drive mechanism and arrange medium vessel 3 below piston 83. Medium inside medium vessel 3 then flows into main culture vessel 2 by means of a first connecting line 5 by opening pinching valve 79, which closes first connecting line 5 between main culture vessel 2 and medium vessel 3, and lowering piston 83. The descent of piston 83 is then stopped and pinching valve 79 is closed again when a predetermined amount of medium has flown into main culture vessel 2. As a result, since cells C are mixed in the medium, primary culturing of cells C is begun by allowing to stand in this state.

Next, case 84 is rotated to arrange main culture vessel 2 below piston 83 at a suitable medium replacement time after a predetermined amount of time has elapsed. The medium inside main culture vessel 2 is then discharged into waste medium vessel 4 by opening pinching valve 80, which closes second connecting line 6 between main culture vessel 2 and waste medium vessel 4, and lowering piston 83. At this time, since cells C are adhered to the bottom of main culture vessel 2, the cells remain in main culture vessel 2 without being discharged into waste medium vessel 4.

Medium inside medium vessel 3 is then supplied to main culture vessel 2 by again rotating case 84 to arrange medium vessel 3 below piston 83, and controlling piston 83 and pinching valve 79. As a result, the medium is replaced.

Following completion of the primary culturing step in which cells are cultured while replacing the medium a plurality of times at predetermined replacement intervals, case 84 is rotated to arrange main culture vessel 2 below piston 83. Medium is then discharged from main culture vessel 2 into waste medium vessel 4 by controlling piston 83 and pinching valve 80. Subsequently, by again rotating case 84 to arrange enzyme vessel 13 below piston 83, and controlling piston 83 and pinching valve 81, trypsin is supplied from enzyme vessel 13 to main culture vessel 2. The trypsin acts on cells C in main culture vessel 2 causing the cells C adhered to the inner walls to be detached.

Case 84 is then rotated at high speed while in this state by closing all pinching valves 79 through 81 and operating the rotary drive mechanism. As a result, cells C suspended in the trypsin within main culture vessel 2 are collected to the outside in the radial direction from the trypsin by centrifugal separation. Since occluded connecting line 17 is arranged to the outside in the radial direction of main culture vessel 2, the separated cells C are collected in occluded connecting line 17.

After then stopping case 84 at the location where main culture vessel 2 is arranged below piston 83, and connecting a second main culture vessel (not shown) in which a bone supplement material is sealed to occluded connecting line 17 by, for example, aseptic tube connection, cells C that have been collected in occluded connecting line 17 can be efficiently transferred to the second main culture vessel.

In this manner, according to culture apparatus 70 as claimed in the present embodiment, the number of pistons 83 of the pressing means can be reduced by causing case 84 to rotate, thereby simplifying the structure. In addition, since main culture vessel 2 is arranged at a location away from axial center of rotation 82 of case 84, and occluded connecting line 17 is provided to the outside in the radial direction of main culture vessel 2 housed in indentation 72 of case 84, centrifuged cells C are collected in occluded connecting line 17, thereby allowing culturing to efficiently continue to a subsequent secondary culturing step.

Furthermore, the shapes of the case and vessels are not limited to those shown in each of the aforementioned embodiments. In addition, although the explanation used the example of providing one each of the vessels, a plurality of medium vessels and waste medium vessels, for example, may be provided instead.

Figure 15:
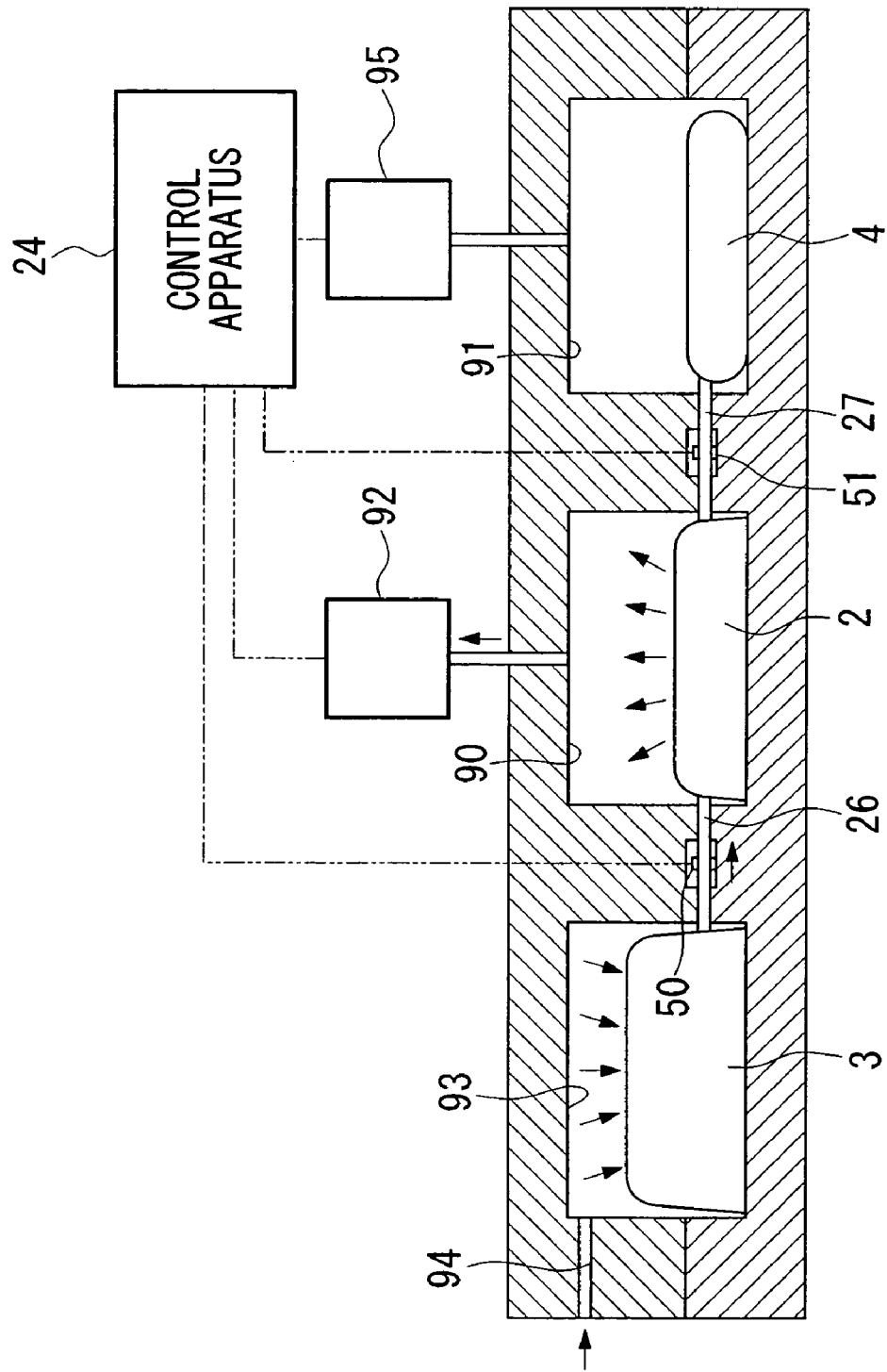
FIG. 15 is a longitudinal cross-sectional view showing a variation of the culture apparatuses of the first, second and third embodiments.

In addition, although the explanations of each of the aforementioned embodiments described a method whereby medium and so forth is transferred by pressing each vessel with a piston on the side on which medium and so forth is discharged, as shown in FIG. 15, a method may alternatively be employed in which each vessel 2 and 4 is arranged in a housing chamber 90 and 91 that are sealed from the outside, and medium and so forth is aspirated by reducing the pressure in said housing chambers 90 and 91 in which the vessels are housed on the side on which medium and so forth is received.

More specifically, as shown in FIG. 15, is order to supply medium to main culture vessel 2, in addition to opening pinching valve 50 that has closed first connecting line 26 by operating control apparatus 24, the pressure within housing chamber 90 in which main culture vessel 2 is arranged is lowered by operating a first vacuum pump 92. Since housing chamber 93 in which medium vessel 3 is housed is made to be open to the atmosphere by communicating holes 94, medium vessel 3 contacts freely resulting in medium being aspirated into main culture vessel 2.

In addition, after a predetermined culturing period has elapsed, in addition to opening a second connecting line 27 by operating pinching valve 57 that had been closing second connecting line 27 by operating control apparatus 24, the pressure inside housing chamber 90 housing main culture vessel 2 is opened to the atmosphere. The pressure in housing chamber 91 in which waste medium vessel 4 is housed is then lowered by operating a second vacuum pump 95. As a result, medium inside main culture vessel 2 is aspirated towards waste medium vessel 4.

FOURTH EMBODIMENT

Culture Apparatus

Next, an explanation is provided of a culture apparatus as claimed in a fourth embodiment of the present invention with reference to the drawings.

Culture apparatus 101 as claimed in the present embodiment is used in the aforementioned culturing process, and particularly in a primary culturing step.

Figure 16:
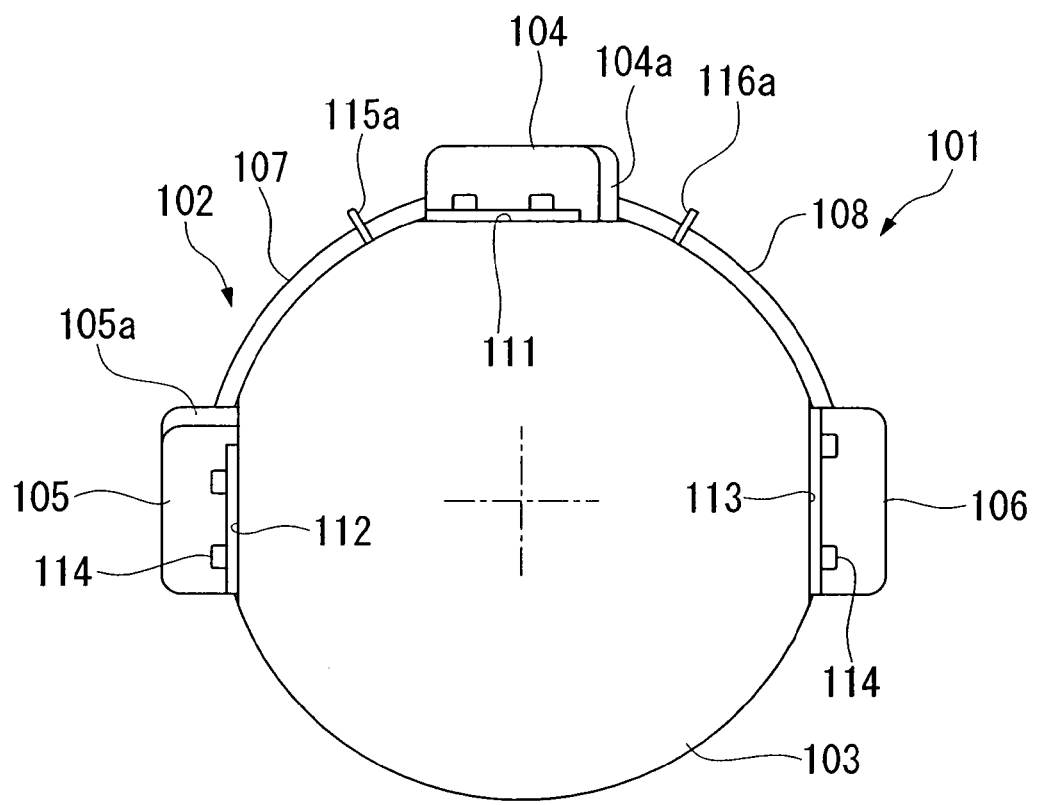
FIG. 16 is a front view showing a culture apparatus as claimed in a fourth embodiment of the present invention.
Figure 17:
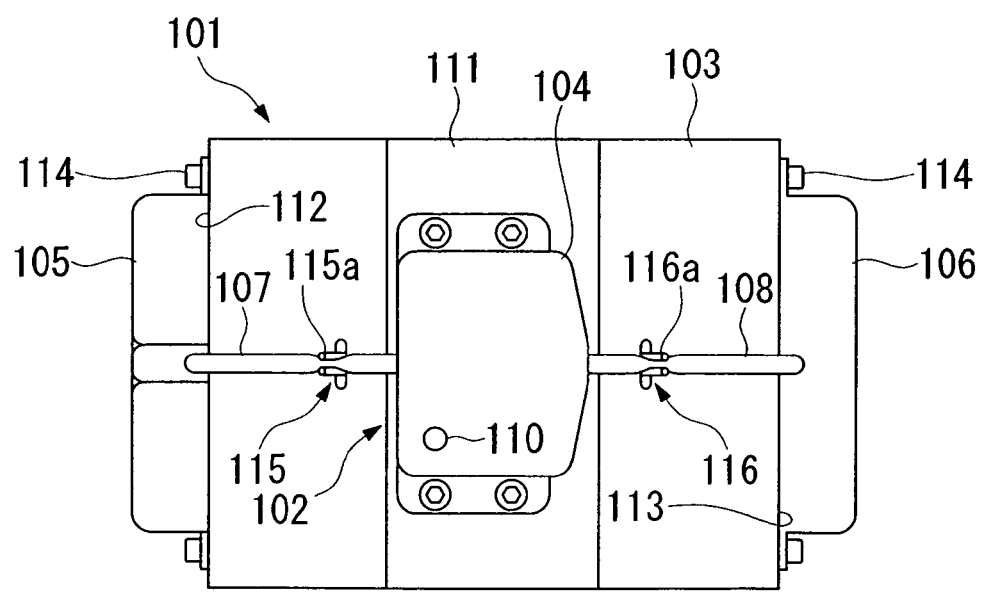
FIG. 17 is a side view of the culture apparatus of FIG. 16.
Figure 18:
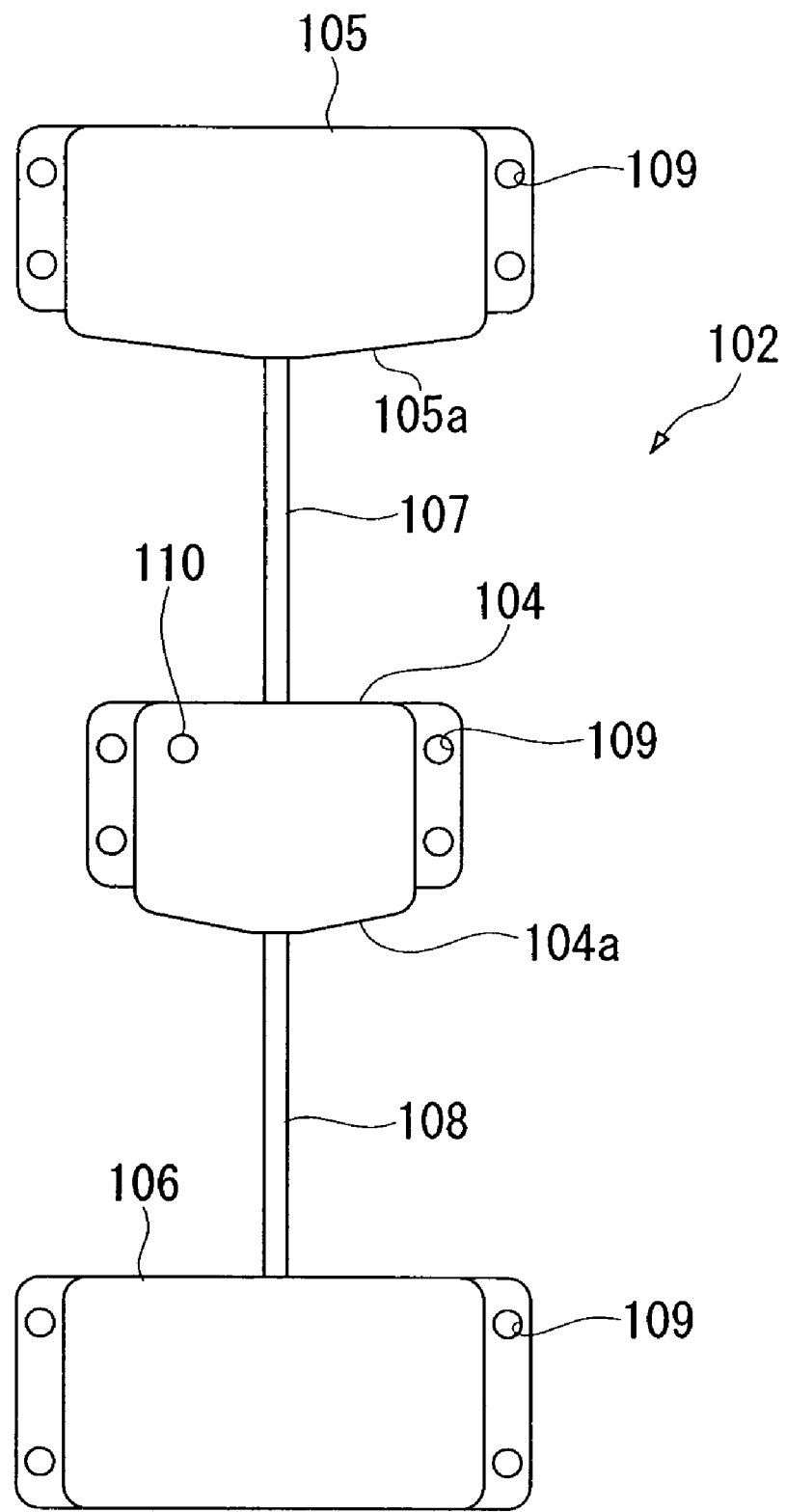
FIG. 18 is a front view showing culture vessels used in the culture apparatus of FIG. 16.

As shown in FIGS. 16 and 17, culture apparatus 101 as claimed in the present embodiment is composed of a culture vessel 102 and a rotary drum (level difference adjustment means) 103 on which said culture vessel 102 is attached to the outer peripheral surface. As shown in FIG. 18, culture vessel 102 is composed of a single main culture vessel 104, a single medium vessel 105, a single waste medium vessel 106, a first connecting line 107 that connects main culture vessel 104 and medium vessel 105, and a second connecting line 108 that connects main culture vessel 104 and waste medium vessel 106.

Main culture vessel 104, medium vessel 105 and waste medium vessel 106 are respectively composed of a material such as hard polystyrene. In addition, first and second connecting lines 107 and 108 are composed of flexible tubes like those made of vinyl chloride. As a result, together with being able to arrange each vessel 104, 105 and 106 at arbitrary locations by bending each connecting line 107 and 108, the flow of fluid inside can be restricted by clamping an intermediate site in the lengthwise direction of connecting lines 107 and 108 with a clip or pinching valve that clamps in the radial direction. Furthermore, prior to being attached to rotary drum 103, first and second connecting lines 107 and 108 are closed by removable clips (not shown), for example, to restrict the flow of fluid.

In addition, medium vessel 105 on the side of main culture vessel 104 and main culture vessel 104 on the side of waste medium vessel 106 are respectively provided with inclined surfaces 105a and 104a to facilitate the flow of fluid within medium vessel 105 into main culture vessel 104 and the flow of fluid within main culture vessel 104 into waste medium vessel 106. In FIG. 18, reference symbol 109 indicates mounting holes for installing each vessel 104, 105 and 106 on rotary drum 103.

In addition, a medium is sealed inside the aforementioned main culture vessel 104 and medium vessel 105 that is prepared with minimum essential medium (MEM), fetal bovine serum (FBS) and antibiotic and so forth at a predetermined blending ratio such as 84:15:1. Human serum may also be used instead of FBS. Any arbitrary antibiotic can be used for the antibiotic, examples of which include penicillin-based, cepham-based, macrolide-based, tetracycline-based, fosfomycin-based, aminoglycoside-based and new quinolone-based antibiotics.

A gas such as $CO_2$ gas at a concentration of 5% is sealed in a sterile state in the aforementioned waste medium vessel 106.

The aforementioned main culture vessel 104 is provided with an injection port 110 that can be penetrated with an injection needle and closes due to elasticity after the injection needle has been removed. As a result, a body fluid such as bone marrow fluid can be injected into main culture vessel 104 by puncturing the injection port 110 with an injection needle of a syringe used to collect bone marrow fluid, and the inside of main culture vessel 104 can be isolated from the outside by retracting the injection needle from injection port 110.

The aforementioned rotary drum 103 has a cylindrical surface centering around the horizontal axis of rotation, and is connected to a rotary drive source like a motor (not shown). In addition, vessel mounting brackets 111, 112 and 113 for installing each of the aforementioned vessels 104, 105 and 106 are provided on the outer surface of the cylindrical surface serving as the outer peripheral surface of rotary drum 103. Vessel mounting bracket 111 of main culture vessel 104 is arranged between vessel mounting bracket 112 of medium vessel 105 and vessel mounting bracket 113 of waste medium vessel 106, and are respectively arranged at intervals in the circumferential direction of rotary drum 103. For example, in the example shown in FIGS. 16 and 17, the mounting brackets are arranged at 90° intervals in the circumferential direction of rotary drum 103.

Each vessel 104, 105 and 106 is installed on rotary drum 103 using, for example, bolts 114. Thumbscrews, belts, hooks or other arbitrary fastening means may also be used instead of bolts 114.

In addition, when each vessel 104, 105 and 106 has been attached to each vessel mounting bracket 111, 112 and 113, pinching valves 115 and 116 that clamp each connecting line 107 and 108 in the radial direction at an intermediate location in the lengthwise direction are provided in the connecting line pathways in which connecting lines 107 and 108 are arranged between vessels 104, 105 and 106. Pinching valves 115 and 116 are provided with two pins 115a and 116a extending to the outside in the radial direction towards the outside of the cylindrical surface from the inside of rotary drum 103, and connecting lines 107 and 108 can be opened and closed by switching the distance of pins 115a and 116a simply by inserting connecting lines 107 and 108 between these pins 115a and 116a. Opening and closing of each pinching valve 115 and 116 is controlled by a controller not shown.

The following provides an explanation of the operation of culture apparatus 101 as claimed in the present embodiment composed in this manner.

In order to culture cells using culture apparatus 101 as claimed in the present embodiment, first bone marrow liquid is injected into main culture vessel 104 by puncturing injection port 110 with a syringe needle of a syringe used to collect bone marrow fluid as previously described.

Rotary drum 103 is then rotated by a predetermined angle, and rotary drum 103 is locked at the position where main culture vessel 104 is positioned horizontally at the highest location. While in this state, culturing is carried out by subjecting main culture vessel 104 to predetermined culturing conditions such as a temperature of $37 \pm 0.5°$ C., humidity of 100% and $CO_2$ concentration of 5%. The $CO_2$ culturing conditions can be achieved by either dissolving $CO_2$ in the medium or composing all or a portion of main culture vessel 104 with a $CO_2$-permeable filter.

Figure 19:
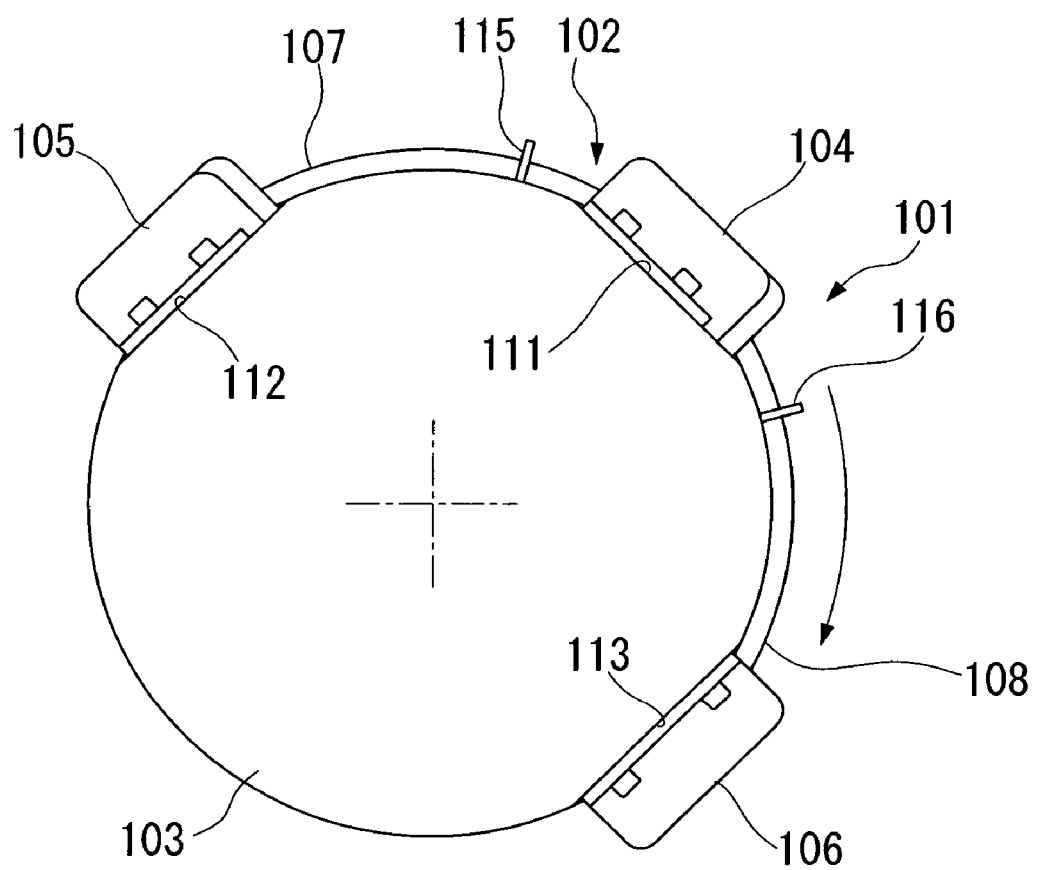
FIG. 19 is a front view showing a step in which medium is discharged from a main culture vessel to a waste medium vessel in the culture apparatus of FIG. 16.

Subsequently, when a predetermined medium replacement time has been reached, as shown in FIG. 19, rotary drum 103 is rotated by a predetermined angle to position main culture vessel 104 at a higher location than medium vessel 106. In the case of the present embodiment, since main culture vessel 104 is arranged at the highest location during culturing, rotary drum 103 does not have to be rotated. However, in order to transfer the medium in main culture vessel 104 to waste medium vessel 106 more smoothly, as shown in FIG. 19 for example, main culture vessel 104 is preferably oriented diagonally upward while waste medium vessel 106 is preferably oriented diagonally downward.

While in this state, pinching valve 116 that had been closing second connecting line 108 is opened. As a result, medium that is no longer necessary is discharged by its own weight from main culture vessel 104 into waste medium vessel 106 through second connecting line 108. When a predetermined amount of medium in main culture vessel 104 has been discharged, pinching valve 116 is operated to again close second connecting line 108.

Figure 20:
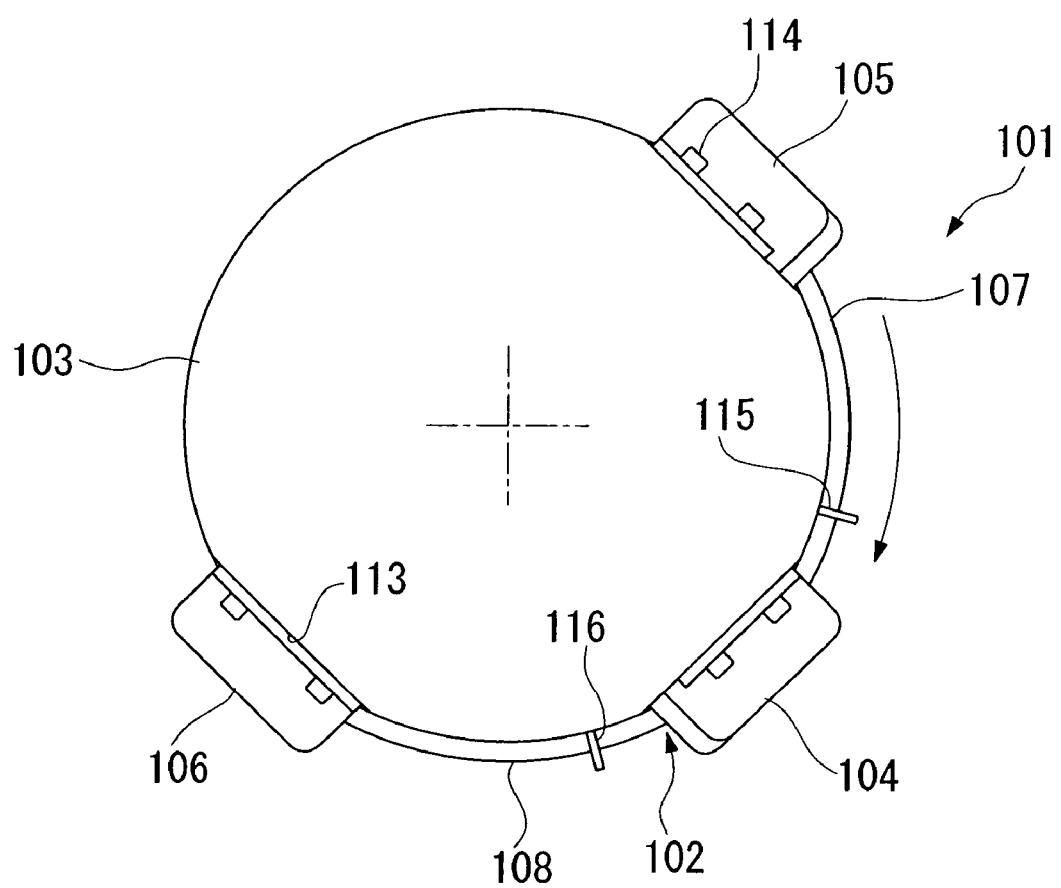
FIG. 20 is a front view showing a step in which medium is supplied from a medium vessel to a main culture vessel in the culture apparatus of FIG. 16.

Next, rotary drum 103 is rotated by a predetermined angle so that main culture vessel 104 is arranged at a lower location than medium vessel 105 as shown in FIG. 20. Namely, main culture vessel 104 is oriented diagonally downward while medium vessel 105 is oriented diagonally upward. Pinching valve 115 that had been closing first connecting line 117 is then opened. As a result, fresh medium is supplied from medium vessel 105 to main culture vessel 104 through first connecting line 117. As a result, since the medium replacement step is completed, rotary drum 103 is rotated by a predetermined angle to return main culture vessel 104 to the highest location and continue culturing.

As a result of continuing culturing while repeating this medium replacement step a plurality of times, mesenchymal stem cells adequately grow on the bottom of main culture vessel 104. Main culture vessel 104 that houses the grown mesenchymal stem cells can be transported independently by sealing with heat and then severing all of the connecting lines 107 and 108 connected to said main culture vessel 104.

In this manner, according to culture apparatus 101 as claimed in the present embodiment, medium and so forth required for culturing can be sealed in advance, and the inside of main culture vessel 102 can be isolated from the outside in a sealed state throughout the culturing period of the primary culturing step. As a result, contamination by dust particles and so forth from the outside can be prevented. In addition, even when replacing the medium during which medium droplets are dispersed easily, medium can be transferred between vessels 104, 105 and 106 by gravity while sealed within each vessel 104, 105 and 106 and connecting lines 107 and 108 simply by rotating rotary drum 103 and arranging each vessel 104, 105 and 106 at a predetermined position. Thus, the effects of contamination by other bacteria from the outside can be eliminated.

Furthermore, although culture vessel 102 in the present embodiment has been explained as being applicable to a primary culturing step in which mesenchymal stem cells are grown while replacing the medium a plurality of times at predetermined times, culture vessel 102 may also be composed to be applicable to a secondary culturing step by sealing a bone supplement material such as a β-tricalcium phosphate porous body in main culture vessel 104 and loading mesenchymal stem cells cultured in a primary culturing step.

In addition, a blood collection line (not shown) may be connected to main culture vessel 104, and bone marrow fluid collected from a patient with said blood collection line may be loaded directly into main culture vessel 104.

In addition, although connecting lines 107 and 108 are opened and closed by pinching valves 115 and 116 provided in rotary drum 103, instead of these pinching valves, opening and closing valves may also be provided directly in connecting lines 107 and 108.

Figure 21:
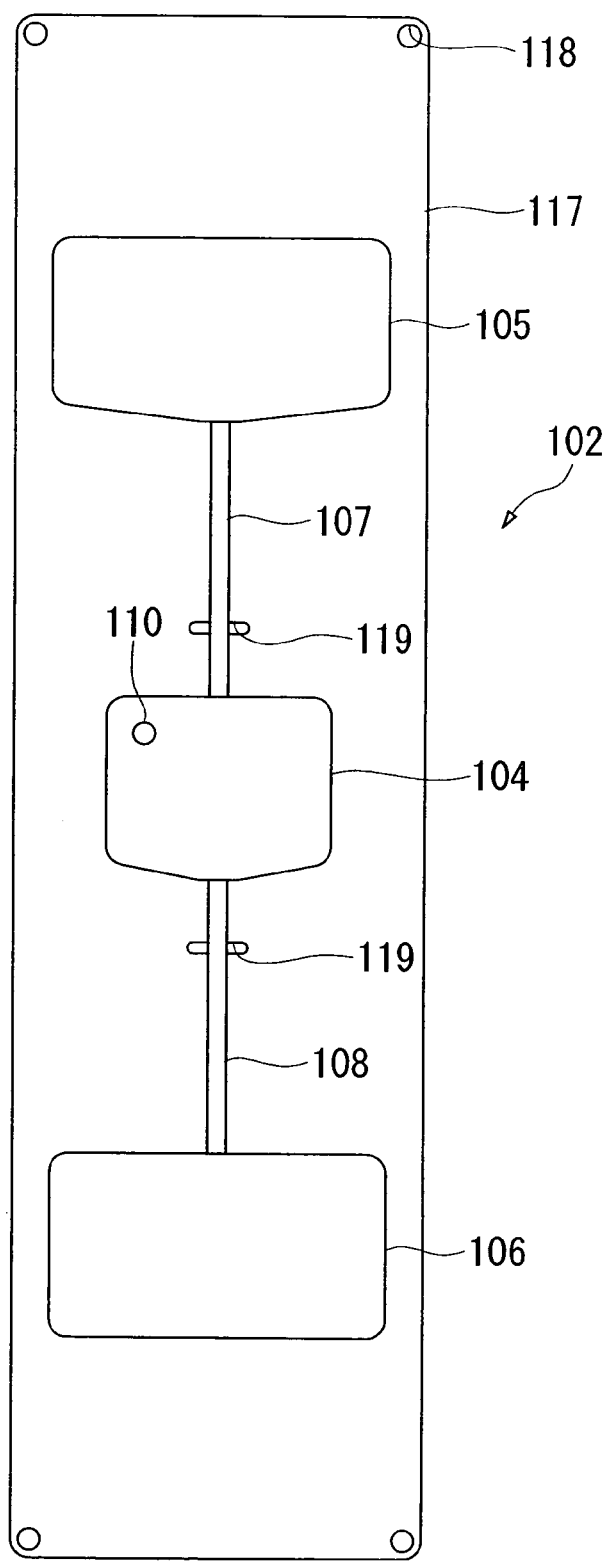
FIG. 21 is a front view showing a variation of the culture vessels in the culture apparatus of FIG. 16.

In addition, although culture apparatus 101 as claimed in the aforementioned embodiment has been explained using the example of culture vessel 102 in which main culture vessel 104, medium vessel 105 and waste medium vessel 106 are mutually connected by connecting lines 107 and 108, as shown in FIG. 21, each culture vessel 104, 105 and 106 and connecting lines 107 and 108 may be integrally attached to a bendable, flexible sheet 117. Bolt mounting holes 118 for attaching to rotary drum 103 and through holes 119 for allowing the pins of pinching valves 115 and 116 to pass through are provided in sheet 117.

Figure 22:
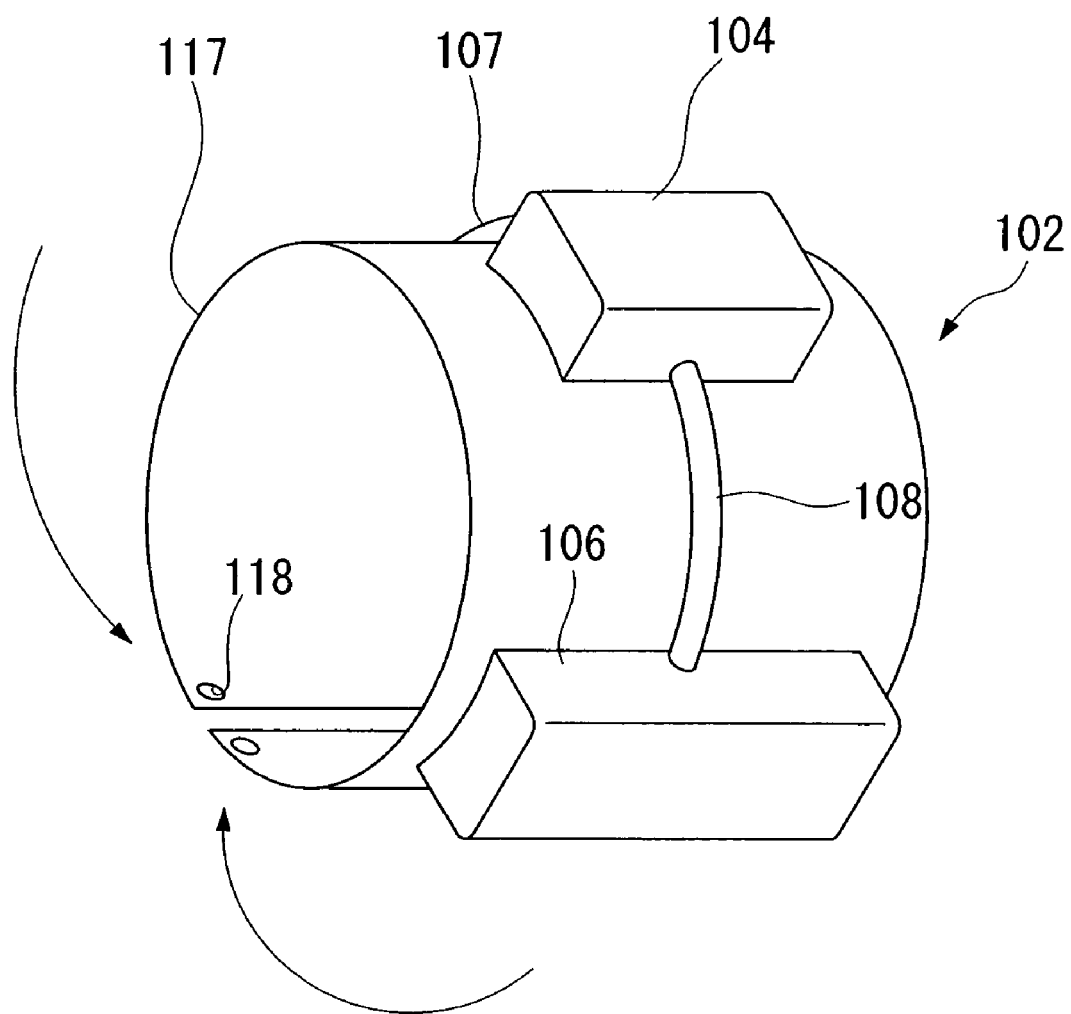
FIG. 22 is a perspective view of the culture vessels shown in FIG. 21.

As a result of being composed in this manner, when attaching culture vessel 102 to rotary drum 103, sheet 117, which integrates each vessel 104, 105 and 106 and connecting lines 107 and 108 into a single unit, is bent into a cylindrical shape as shown in FIG. 22 and attached to the outer surface of rotary drum 103. Thus, the need to position each vessel 104, 105 and 106 and connecting lines 107 and 108 can be eliminated, thereby facilitating mounting work.

FIFTH EMBODIMENT

Culture Apparatus

Figure 23:
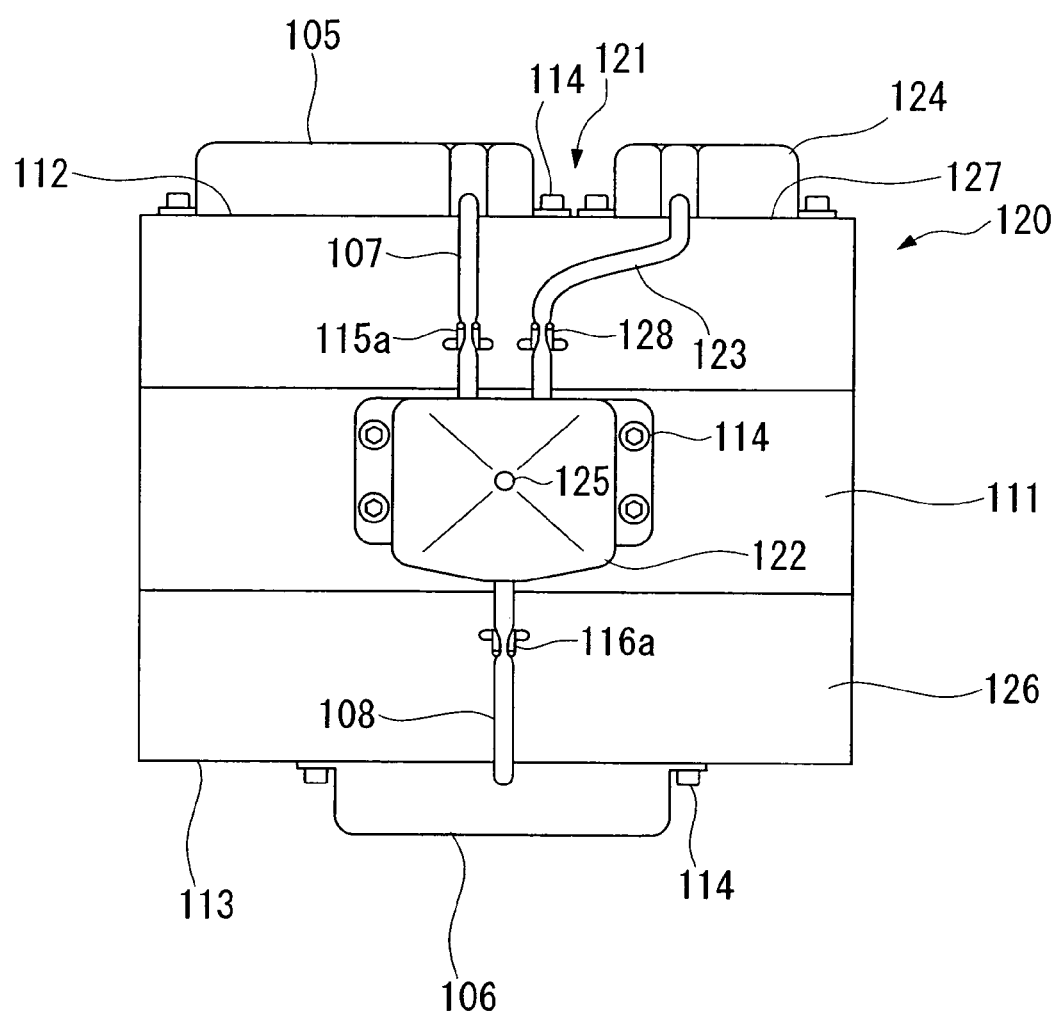
FIG. 23 is a side view showing a culture apparatus as claimed in a fifth embodiment of the present invention.

Next, an explanation is provided of a culture apparatus as claimed in a fifth embodiment of the present invention with reference to FIG. 23.

Furthermore, in the explanation of culture apparatus 120 as claimed in the present embodiment, the same reference symbols are used for those locations in the present embodiment that are the same as the constitution of culture apparatus 101 as claimed in the aforementioned fourth embodiment, and their explanations are omitted.

As shown in FIG. 23, culture vessel 121 of culture apparatus 120 as claimed in the present embodiment differs from culture vessel 102 in the aforementioned fourth embodiment in that it is provided with an enzyme vessel 124 connected to main culture vessel 122 by means of a third connecting line 123, and in that a cell recovery line 125 is provided for main culture vessel 122.

A protease enzyme such as trypsin is sealed in enzyme vessel 124, and third connecting line 123 is occluded by a removable clip. Enzyme vessel 124 is installed on a rotary drum 126 arranged in a row in the lengthwise direction, for example, at the same position in the circumferential direction as medium vessel 105.

In addition to a vessel mounting bracket 127 for installing enzyme vessel 124 being provided on rotary drum 126, a pinching valve 128 is provided that occludes third connecting line 123 by clamping in the radial direction when enzyme vessel 124 has been installed.

Figure 24:
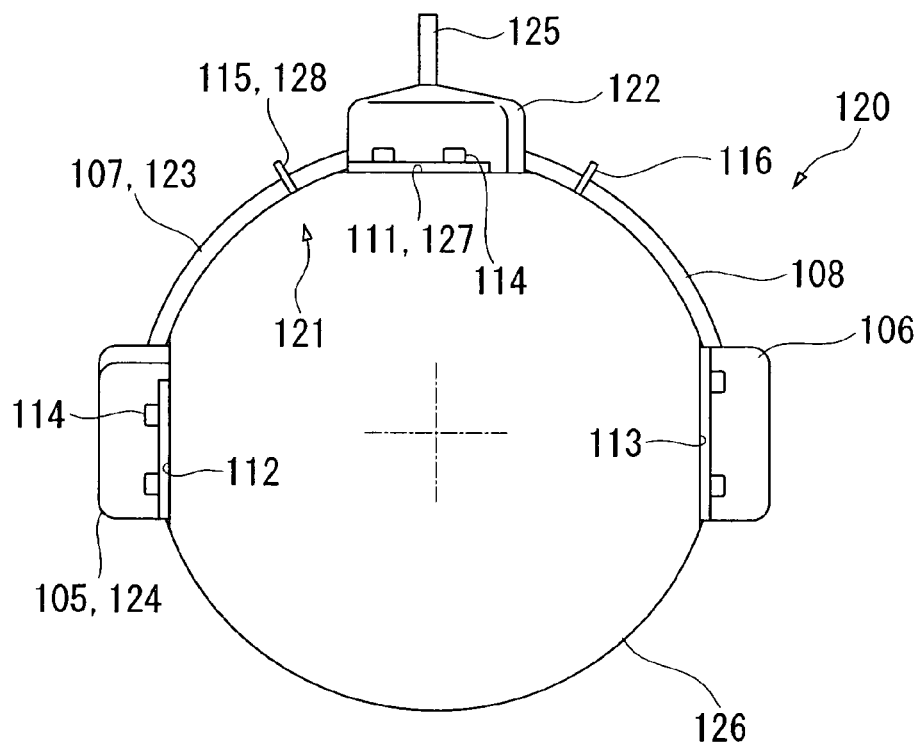
FIG. 24 is a front view of the culture apparatus shown in FIG. 23.

The aforementioned cell recovery line 125 is provided in the center of the surface arranged to the outside in the radial direction when main culture vessel 122 is attached to rotary drum 126. In addition, as shown in FIG. 24, the surface of main culture vessel 122 on which this cell recovery line 125 is provided is formed into the shape of a funnel that gradually narrows from the periphery towards cell recovery line in the center. Cell recovery line 125 is composed of a vinyl chloride or other flexible tube in the same manner as connecting lines 107, 108 and 123, and is in the form of an occluded tube, the end of which is occluded.

The following provides an explanation of the operation of culture apparatus 120 as claimed in the present embodiment composed in this manner.

The operation until cells are cultured while periodically replacing the medium is the same as culture apparatus 101 as claimed in the fourth embodiment.

According to culture apparatus 120 as claimed in the present embodiment, after mesenchymal stem cells have grown in an adhered state in main culture vessel 122, by rotating rotary drum 126 by a predetermined angle, main culture vessel 122 is arranged diagonally upward while waste medium vessel 106 is arranged diagonally downward. By then operating pinching valve 116 that had been closing second connecting line 108 to open second connecting line 108, a predetermined amount of medium to be discharged in main culture vessel 122 is discharged to waste medium vessel 106 by gravity.

Subsequently, enzyme vessel 124 is then positioned at a higher location that main culture vessel 122 by again rotating rotary drum 126 by a predetermined angle. By then opening third connecting line 123 by operating pinching valve 128 that has been closing third connecting line 123, trypsin stored in enzyme vessel 124 is supplied by gravity to main culture vessel 122 through third connecting line 123.

Mesenchymal stem cells that had been adhered to the bottom of main culture vessel 122 are then detached by allowing to stand for a predetermined amount of time or applying vibrations to main culture vessel 122 by rocking rotary drum 126 in the state in which third connecting line 123 is again closed by operating pinching valve 128. As a result, the detached mesenchymal stem cells are mixed in fluid consisting of trypsin and medium in a state in which the adhesion between cells has been severed.

Subsequently, the medium containing mesenchymal stem cells and trypsin in main culture vessel 122 is then centrifuged by continuously rotating rotary drum 126 in a single direction. Since the mesenchymal stem cells have a higher specific gravity than the trypsin and other substances, the cells are spun to the outside in the radial direction as a result of centrifugation.

According to culture apparatus 120 as claimed in the present embodiment, since main culture vessel 122 is formed in the shape of a funnel, mesenchymal stem cells that have been spun to the outside in the radial direction are gathered in the center by the funnel-shaped vessel walls. Since cell recovery line 125 is provided in the center, the gathered mesenchymal stem cells are recovered in cell recovery line 125.

In addition, since this cell recovery line 125 is composed of vinyl chloride that can be sealed or fused by heat, severed end 125a can be occluded together with severing cell recovery line 125 by aseptic tube severing. Namely, as shown in FIG. 8A, severed end 125a can be occluded by using a heating plate 129 that moves in the direction of shearing as shown in FIG. 8A, severing while melting as shown in FIG. 8B, and occluding the severed end while maintaining the inside of the connecting tube in a sterile and sealed state as shown in FIG. 8C.

In addition, aseptic tube connection can also be carried out as shown in FIGS. 9A through 9C. Namely, cell recovery line 125 can be connected to another connecting line 130 by simultaneously severing cell recovery line 125 and another connecting line 130 arranged in parallel as shown in FIG. 9A followed by shifting the lines so that cell recovery line 125 aligns with the other connecting line 130 as shown in FIG. 9B, and then removing heating plate 129 as shown in FIG. 9C. Although the joined portion 17b is occluded during connection, the internal flow path is able to be continuous while the line walls are connected by an external force. Namely, cell recovery line 125 and another connecting line 130 can be connected while maintaining the inside in a sterile state.

Namely, by connecting cell recovery line 125 in which mesenchymal stem cells have been recovered to connecting line 130, which is linked to another main culture vessel (not shown) in which a body tissue supplement material is sealed, by aseptic tube connection, culturing of the recovered mesenchymal stem cells can be continued in a secondary culturing step in a aseptic state.

Furthermore, since mesenchymal stem cells are present inside cell recovery line 125, a spare space 131 for severing may be formed in the end of cell recovery line 125 as shown in FIG. 10 since there is the risk of the mesenchymal stem cells being damaged by heating plate 129. Namely, by severing along cross-sectional line A that passes through spare space 131, heating plate 129 is prevented from making direct contact with mesenchymal stem cells in cell recovery line 125, thereby making it possible to carry out aseptic tube connection while maintaining the viability of the mesenchymal stem cells.

Furthermore, although enzyme vessel 124 is provided and the mesenchymal stem cells are detached by trypsin in the present embodiment, temperature-responsive treatment switching between hydrophilic and hydrophobic properties bordering on a predetermined temperature may be carried out on the inner walls of main culture vessel 122 instead of using trypsin. This temperature-responsive treatment is the same as that previously described.

SIXTH EMBODIMENT

Culture Apparatus

Next an explanation is provided of a culture apparatus 140 as claimed in a sixth embodiment of the present invention with reference to the drawings.

Figure 25:
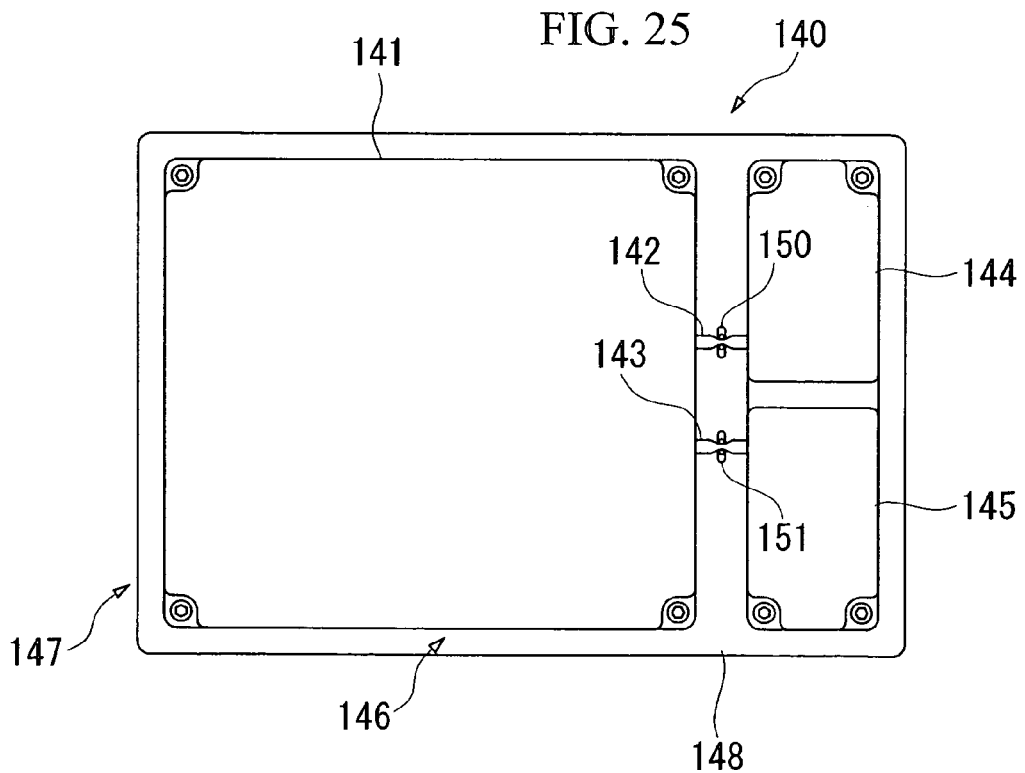
FIG. 25 is an overhead view showing a culture apparatus as claimed in a sixth embodiment of the present invention.
Figure 26:
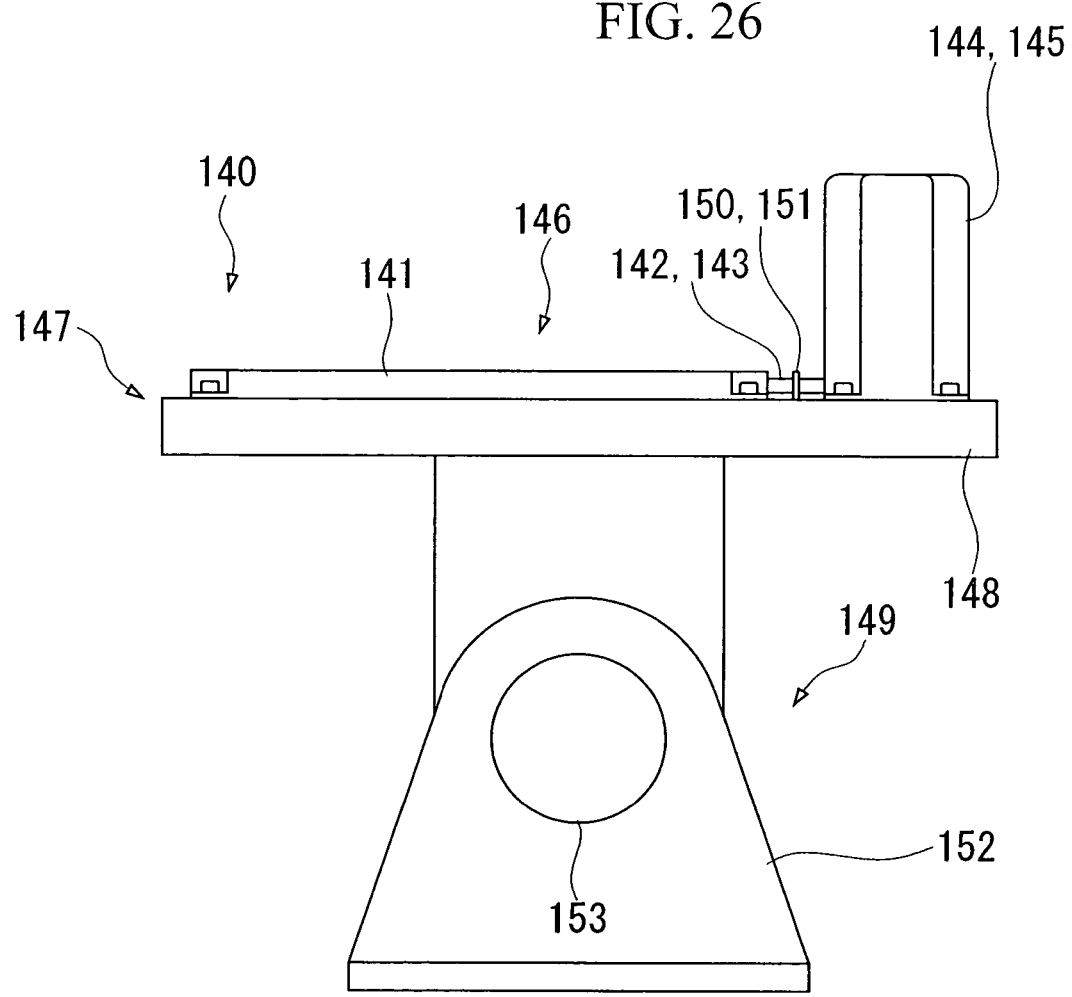
FIG. 26 is a front view of the culture apparatus shown in FIG. 25.

As shown in FIGS. 25 and 26, this culture apparatus 140 as claimed in the present embodiment is provided with a main culture vessel 141, a culture vessel 146 having a medium vessel 144 and a waste medium vessel 145 connected to said main culture vessel 141 by means of connecting lines 142 and 143, and a mounting frame (level difference adjustment means) 147 on which said culture vessel 146 is installed and which changes its inclination angle.

The aforementioned main culture vessel 141 is formed in the shape of a flat, thin box that has a comparatively large bottom surface area. The aforementioned medium vessel 144 and waste medium vessel 145 are formed in the shape of boxes having a larger height than main culture vessel 141, while also having an inner volume that is several times the inner volume of main culture vessel 141. This medium vessel 144 and waste medium vessel 145 are disposed on the same side of main culture vessel 141.

In addition, medium similar to that previously described is sealed in main culture vessel 141 and medium vessel 144, while the inside of waste medium vessel 145 is empty.

The aforementioned mounting frame 147 is provided with a tray section 148 that immobilizes culture vessel 146, and an oscillating device 149 that rocks said tray section 148 about the horizontal axis. Pinching valves 150 and 151 similar to the fourth embodiment are provided in tray section 148, and are capable of opening and closing connecting lines 142 and 143 by clamping in the radial direction intermediate locations in the lengthwise direction of each connecting line 142 and 143. Oscillating device 149 is provided with a base 152 and a motor 153 that rocks tray section 148 relative to base 152.

The following provides an explanation of the operation of culture apparatus 140 as claimed in the present embodiment composed in this manner.

In order to culture cells using culture apparatus 140 as claimed in the present embodiment, bone marrow cells are first supplied to main culture vessel 141, tray section 148 is made to be level, and the cells are cultured under predetermined culturing conditions similar to those indicated in the previous embodiments while maintaining the bottom of main culture vessel 141 level.

Figure 27:
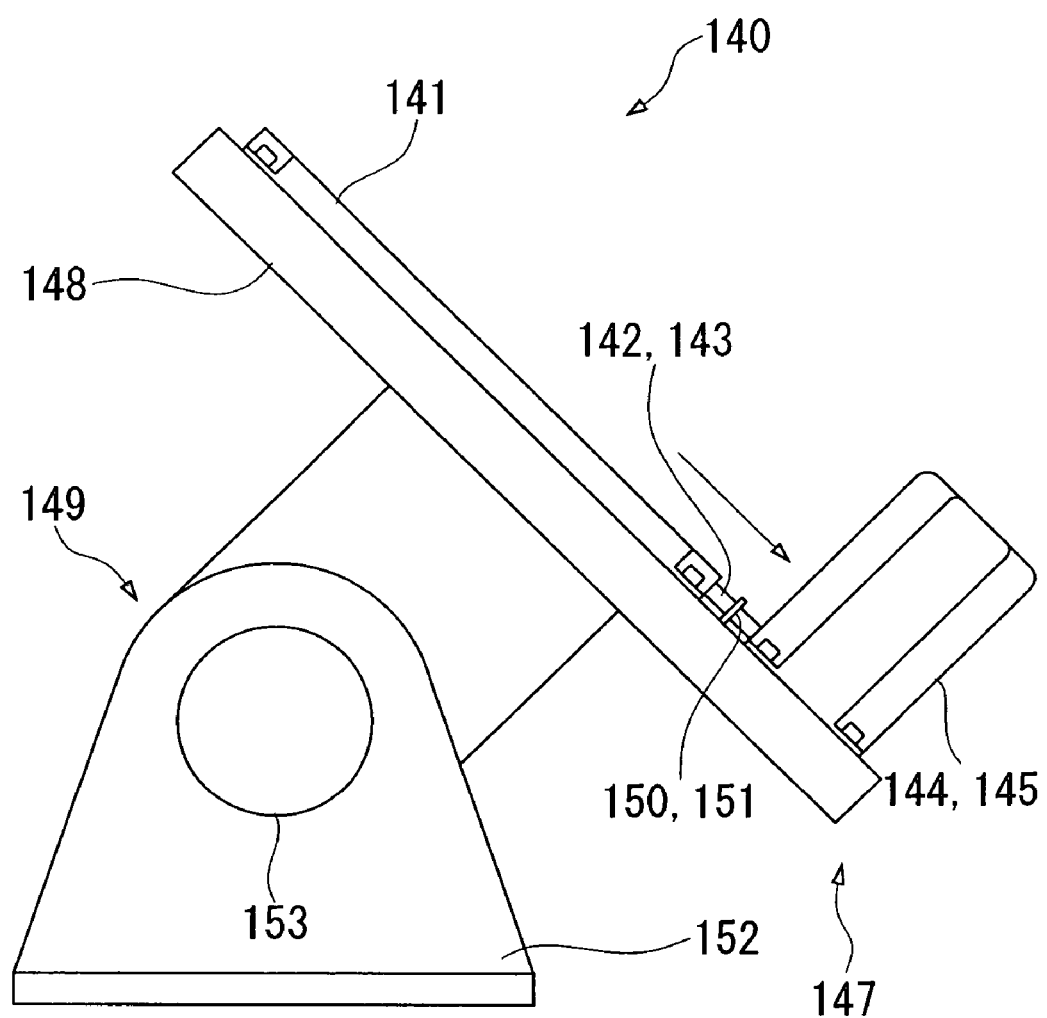
FIG. 27 is a front view showing a step in which medium is discharged from a main culture vessel to a waste medium vessel in the culture apparatus of FIG. 25.

When a predetermined medium replacement time has been reached, by operating motor 153 of mounting frame 147 and rocking tray section 148 relative to base 152, main culture vessel 141 is disposed at a higher position than waste medium vessel 145 as shown in FIG. 27.

While in this state, pinching valve 151 of pinching valves 150 and 151 provided in tray section 148, which had been closing connecting line 143 that connects main culture vessel 141 and waste medium vessel 145, is then opened. As a result, medium to be discarded in main culture vessel 141 is discharged by gravity into waste medium vessel 145. Since adhesive mesenchymal stem cells remain adhered to the bottom surface within main culture vessel 141, connecting line 143 is again closed by operating the aforementioned pinching valve 151.

Figure 28:
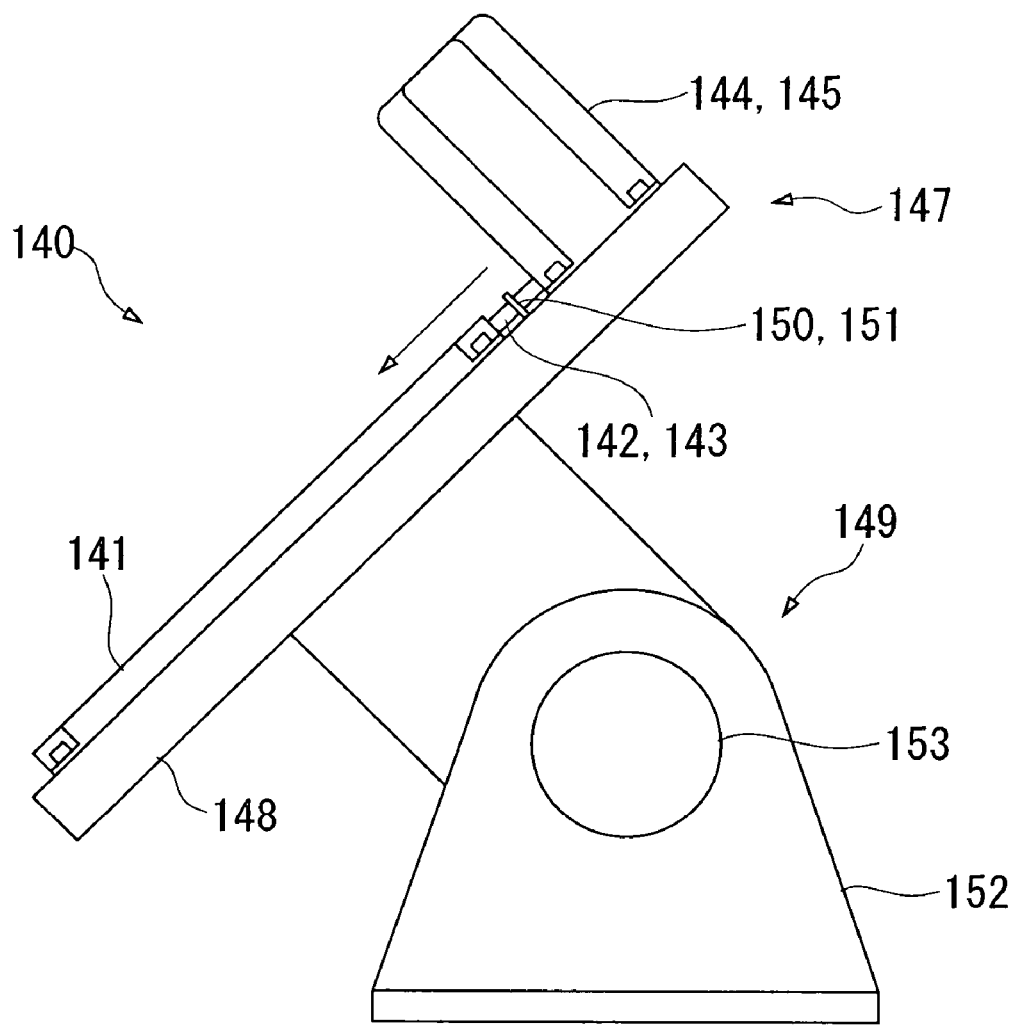
FIG. 28 is a front view showing a step in which medium is supplied from a medium vessel to a main culture vessel in the culture apparatus of FIG. 25.

Subsequently, motor 153 of mounting frame 147 is operated to dispose medium vessel 144 at a higher position than main culture vessel 141 as shown in FIG. 28. Pinching valve 150, which had been closing connecting line 142 that connects main culture vessel 141 and medium vessel 144, is then opened. As a result, fresh medium sealed in medium vessel 144 is supplied by gravity to main culture vessel 141. As a result, since the medium within main culture vessel 141 is replaced with fresh medium, medium replacement is completed by again closing pinching valve 150.

As a result of continuing culturing while repeating this medium replacement step a plurality of times, mesenchymal stem cells are grown to the required number on the bottom surface of main culture vessel 141. Following completion of culturing, main culture vessel 141 can be transported independently in a state in which mesenchymal stem cells are sealed inside by severing connecting lines 142 and 143 by aseptic tube severing.

In this manner, according to culture apparatus 140 as claimed in the present embodiment, cells can be grown to a required number in an aseptic state by replacing the medium in main culture vessel 141 simply by rocking tray section 148. In addition, since cells are cultured in culture vessel 146 while sealed from the outside, contamination by other bacteria and so forth from the outside can be prevented. Moreover, costs can be reduced and operation simplified as a result of employing a simple constitution involving simply rocking tray section 148.

In addition, since main culture vessel 141 is formed into the shape of a thin box to achieve the minimum required medium depth, the amount of medium used can be reduced.

In addition, since each vessel 141, 144 and 145 as well as connecting lines 142 and 143 are installed in a flat tray section 148, their installation work is made easy.

Furthermore, although medium vessel 144 and waste medium vessel 145 are linked to the same side of main culture vessel 141 in the present embodiment, they may also be linked on different sides or on the top and bottom instead. In this case, it is necessary to provide a mechanism that rocks tray section 148 so that a level difference is formed between main culture vessel 141 and medium vessel 144 or waste medium vessel 145 attached to it. In addition, an enzyme vessel or other vessel may also be connected to main culture vessel 141.

In addition, cultured mesenchymal stem cells may be centrifuged in main culture vessel 141 by providing a rotary mechanism that rotates tray section 148 about its normal axis. Moreover, an occluded connecting line for recovering centrifuged mesenchymal stem cells or transferring them to another culture vessel may be provided on one side of main culture vessel 141.

In addition, since each vessel 141, 144 and 145 can be separated by performing aseptic tube severing on connecting lines 142 and 143, symbols, and particularly bar codes, which indicate that the vessels are mutually related vessels, may be affixed to each vessel 141, 144 and 145 to prevent the relationship between the cultured mesenchymal stem cells, the discarded medium and so forth from becoming unclear as a result of the aforementioned separation. The bar codes may be identical bar codes or mutually correlated bar codes.

In addition, a portion or all of main culture vessel 141 may be composed to be transparent, and an observation window (not shown) may be formed in tray section 148 in which main culture vessel 141 is mounted. According to this, culturing status can be observed with, for example, an inverted microscope through an observation window during the culturing period.

Furthermore, in the aforementioned fourth through sixth embodiments, the shapes of rotary drums 103 and 126, mounting frame 147 and vessels 104, 105, 106, 122, 124, 141, 144 and 145 are not limited to those indicated in each of the aforementioned embodiments. In addition, although the previous explanations have used the example of providing one each of vessels 104, 105, 106, 122, 124, 141, 144 and 145, a plurality of, for example, medium vessels 105 and 144 or waste medium vessels 106 and 145 may be provided instead. In addition, in addition to these vessels 104, 105, 106, 122, 124, 141, 144 and 145, in the case of a secondary culturing step for example, a vessel in which is sealed a differentiation induction factor such as dexamethasone may be connected in advance, or may be connected by aseptic tube connection.

Furthermore, although the cultured cells in each of the aforementioned embodiments were explained by using the example of mesenchymal stem cells, the present invention may also be applied to the case of culturing other cells instead, examples of which include ES cells, somatic stem cells, osteocytes, chondrocytes and neurocytes.

In addition, in addition to bone marrow fluid, peripheral blood or placental blood may be used for the liquid supplied to the main culture vessel. In addition, only bone marrow cells, obtained by centrifuging collected bone marrow fluid, may be supplied to the main culture vessel.

In addition, although the body tissue supplement material was explained by using the example of a bone supplement material composed of β-tricalcium phosphate, any arbitrary biocompatible material such as ceramics, collagen or polylactic acid may be used.

INDUSTRIAL APPLICABILITY

According to the culture vessel and culture apparatus as claimed in the present invention, cells can be cultured while replacing the medium a plurality of times in a culture vessel that is occluded from the outside. As a result, cells can be cultured in a viable state without the cultured cells being contaminated by dust particles and so forth from the outside.

In addition, since the cells are sealed in a vessel, there is no risk of intermixing even if a plurality of types of cells are cultured simultaneously in close proximity, thereby improving culturing efficiency.

The invention claimed is:

1. A culture apparatus comprising:
   a culture vessel comprising:
   a main culture vessel,
   at least one medium vessel in which a medium is sealed, and
   at least one waste medium vessel capable of receiving and housing fluid from the main culture vessel,
   a case provided wit indentations for housing each vessel that composes the culture vessel,
   connecting lines being capable of restricting the flow of fluid between the vessels only in one direction, being made of a flexible material, passing through a connecting line pathway disposed in the case, and comprising:
      a first connecting line that provides fluid connection only in the direction from the medium vessel to the main culture vessel, and
      a second connecting line that provides fluid connection only in the direction from the main culture vessel to the waste medium vessel,
   controlling device including cheek valves and allowing a fluid within the vessels that compose the culture vessel to flow into the connecting lines provided in said vessels, and a pressing device that contracts each vessel housed in the indentations by applying external pressure, wherein said main culture vessel and said medium vessel being sealed from the outside by the connecting lines, each vessel that composes the culture vessel has a variable inner volume, and the flow of fluid within the connecting lines is restricted by clamping the lines by the valve disposed in the connecting line pathways in the radial direction.

2. A culture apparatus according to claim 1, wherein a centrifuge is provided that rotates the case with the culture vessel inside, and the indentations that house the main culture vessels are disposed at intervals from the axis of rotation.

3. A culture apparatus according to claim 1, wherein an occluded connecting line having an occluded end is provided on the main culture vessel, the occluded connecting line is made of a material that can be sealed or fused with heat, the case is provided with a centrifuge that rotates the case with culture vessels inside, and the occluded connecting line is disposed outward in the radial direction of the main reaction vessel centered about the center of the axis of rotation in the state in which the main culture vessel is housed in indentations of the case.

* * * * *